United States Patent [19]

Umezawa et al.

[11] 4,303,785

[45] Dec. 1, 1981

[54] ANTITUMOR ANTHRACYCLINE ANTIBIOTICS

[75] Inventors: Hamao Umezawa; Tomio Takeuchi; Hiroshi Naganawa; Kuniaki Tatsuta, all of Tokyo, Japan

[73] Assignee: Zaidan Hojin Biseibutsu Kagaku Kenkyu Kai, Tokyo, Japan

[21] Appl. No.: 117,163

[22] Filed: Jan. 31, 1980

Related U.S. Application Data

[63] Continuation-in-part of Ser. No. 928,627, Jul. 27, 1978, abandoned.

[30] Foreign Application Priority Data

Aug. 5, 1978 [JP] Japan .................................. 53-94348
Feb. 3, 1979 [JP] Japan .................................. 54-11702
Aug. 31, 1979 [JP] Japan .................................. 54-110255

[51] Int. Cl.³ ...................... C07H 15/24; A61K 31/71
[52] U.S. Cl. .................................... 536/17 A; 424/180
[58] Field of Search ...................... 424/180; 536/17 A

[56] References Cited

U.S. PATENT DOCUMENTS

| 3,590,028 | 6/1971 | Arcamone et al. | 536/17 A |
| 3,616,242 | 10/1971 | Belloc et al. | 195/80 |
| 3,803,124 | 4/1974 | Arcamone et al. | 536/17 A |
| 4,012,448 | 3/1977 | Smith et al. | 536/17 A |
| 4,020,270 | 4/1977 | Arcamone et al. | 536/17 A |
| 4,025,623 | 5/1977 | Arcamone et al. | 536/17 A |

FOREIGN PATENT DOCUMENTS 1003383 9/1965 United Kingdom ............. 536/17 A

*Primary Examiner*—Johnnie R. Brown
*Attorney, Agent, or Firm*—David M. Morse

[57] ABSTRACT

New anthracycline derivatives of adriamycin and daunomycin prepared by the etherification of the C-4' and-/or C-14 hydroxyl groups of the starting material glycosides are found to be useful antimicrobial and antitumor agents.

60 Claims, 14 Drawing Figures

FIG. II

ANTITUMOR ANTHRACYCLINE ANTIBIOTICS

CROSS-REFERENCE TO RELATED APPLICATION

This application is a continuation-in-part application of our prior, copending application Ser. No. 928,627 filed July 27, 1978, now abandoned.

BACKGROUND OF THE INVENTION

1. Field of the Invention

This invention relates to new anthracycline glycoside antibiotics, to methods for their use as antimicrobial and antitumor agents, to pharmaceutical compositions containing them and to methods for the preparation and recovery of said new compounds.

2. Description of the Prior Art

A number of anthracycline glycosides have been disclosed in the literature. Among them, daunomycin (U.S. Pat. No. 3,616,242; U.K. Pat. No. 1,003,383) and adriamycin (U.S. Pat. Nos. 3,590,028 and 3,803,124), which are obtained from the cultured broth of certain streptomyces, have a broad antitumor spectrum against various experimental tumors and are used clinically as potent chemotherapeutic agents. Despite the usefulness of adriamycin and daunomycin as clinical antitumor agents, it is known that they have severe side effects such as alopecia, leukopenia and cardiotoxicity.

The present inventors have extensively studied the chemical modification of daunomycin and adriamycin with the goal of preparing new derivatives of these glycosides having increased anticancer activity and reduced toxicity (side effects). By the present invention, they have succeeded in providing new ether derivatives of adriamycin and daunomycin which possess the desired high antitumor activity and low toxicity.

SUMMARY OF THE INVENTION

This invention relates to certain novel anthracycline glycoside derivatives having the general structural formula

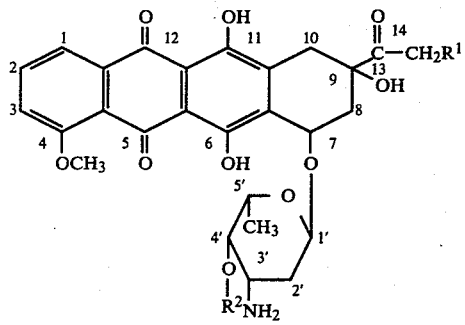

wherein $R^1$ represents hydrogen, hydroxyl, tetrahydropyranyloxy, $C_2$-$C_7$ alkanoyloxy or phenylacetyloxy and $R^2$ represents hydrogen, $C_1$-$C_8$ alkyloxyethyl, cyclohexyloxyethyl, tetrahydrofuranyl, tetrahydropyranyl, 6-methoxytetrahydropyranyl, 6-carbomethoxytetrahydropyranyl or 6-acetoxymethyl tetrahydropyranyl, with the provisos that (1) when $R^1$ is hydrogen or hydroxyl, $R^2$ is not hydrogen and (2) when $R^1$ is tetrahydropyranyloxy, $R^2$ is hydrogen or tetrahydropyranyl, and the nontoxic acid addition salts thereof. The compounds included within the scope of formula I exhibit both antimicrobial and antitumor activity.

As used herein and in the claims the term "nontoxic acid addition salt" is meant to include all those organic and inorganic acid salts of the compounds of formula I, which salts are commonly used as substantially nontoxic salts of medicinal agents containing amine functions. Illustrative examples would be those salts formed from such acids as sulfuric, phosphoric, hydrochloric, hydrobromic, nitric, phosphorous, acetic, propionic, maleic, oleic, palmitic, citric, succinic, tartaric, fumaric, glutamic, pantothenic, laurylsulfonic, methanesulfonic, naphthalenesulfonic, etc.

The 4'-etherified compounds of formula I may exist as the individual diastereomers (arbitrarily designated herein as isomer a and isomer b) or as mixtures of such isomers. The relationship between the structures of isomer a and isomer b is considered to be the difference in absolute configuration R and S of the chiral center of the 4'-O-substituted ether groups since both isomers respectively have different chemical shifts of the methine proton of the chiral center. The present invention specifically includes the separated diastereomers as well as the diatereomeric mixtures within its scope.

DETAILED DESCRIPTION

Figure 1:
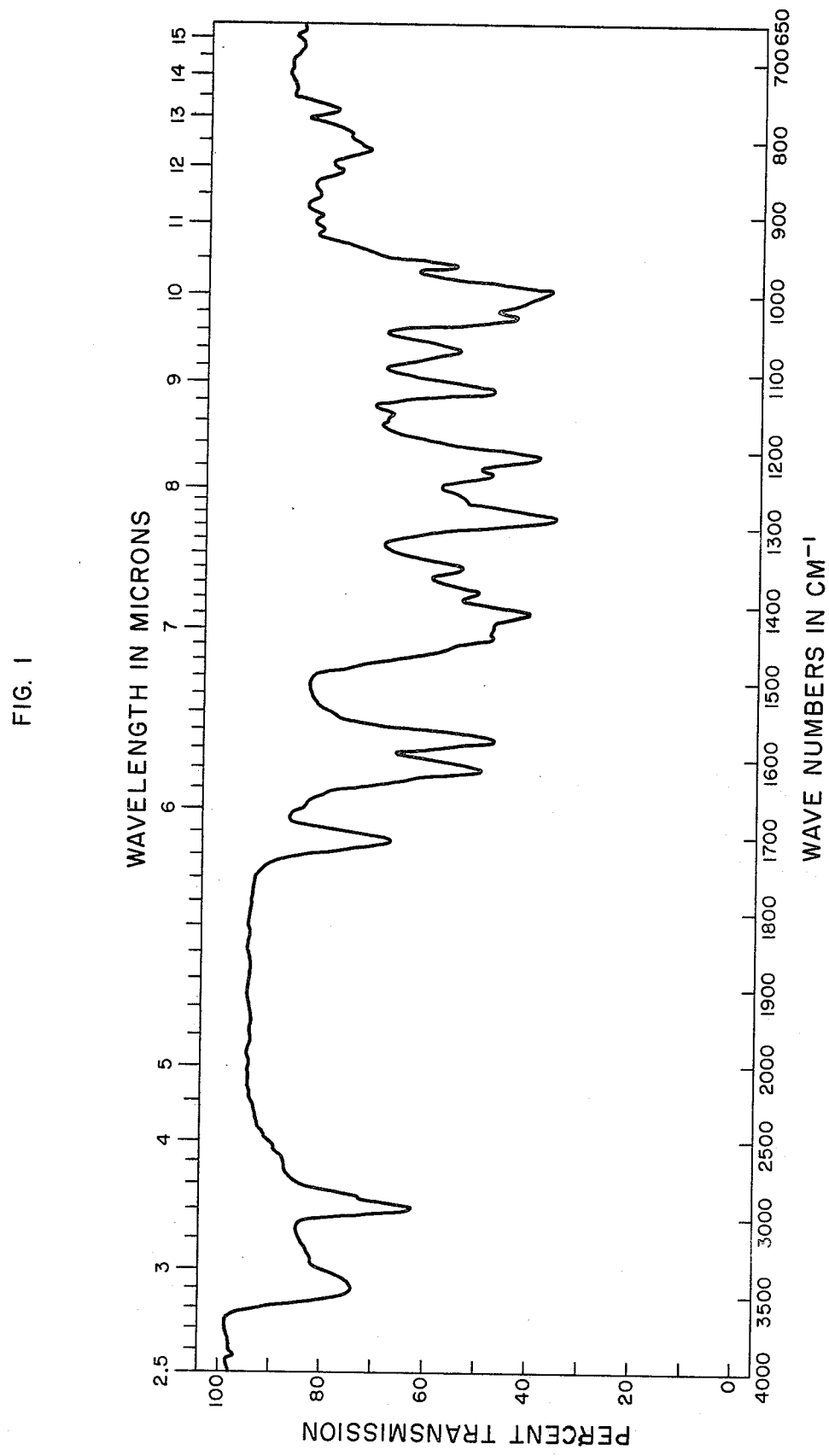
FIG. 1 shows the infrared absorption spectrum (KBr) of 4'-O-tetrahydropyranyl daunomycin (isomer a).

Adriamycin and daunomycin, the starting materials for preparing the compounds of the present invention, may be represented by the formulae

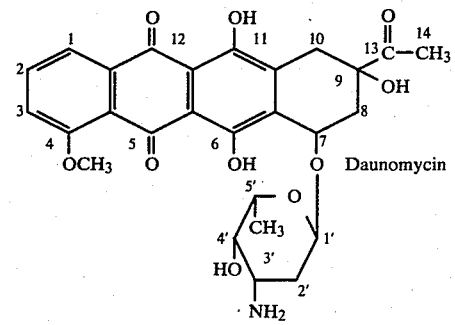

and

-continued

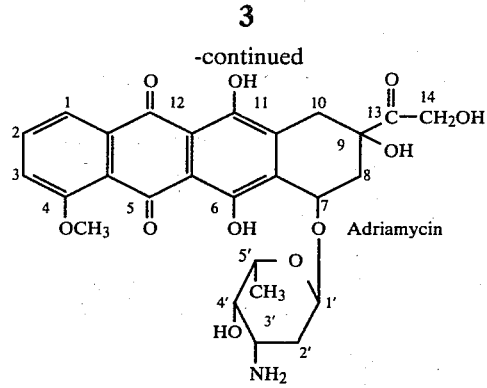
Adriamycin

Starting material glycosides of the formula

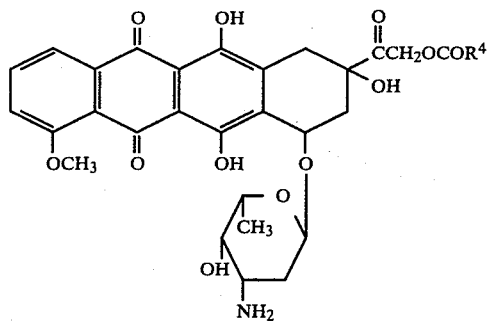

wherein $R^4$ is $C_1$–$C_6$ alkyl (straight or branched chain) or benzyl may be prepared by the method disclosed in U.S. Pat. No. 3,803,124.

Daunomycin possesses two reactive hydroxyl groups (excluding the two phenolic hydroxyl groups) at C-9 and C-4' and adriamycin has three reactive hydroxyl groups (again excluding the two phenolic groups) at C-9, C-14 and C-4'. The present inventors have discovered that under proper conditions there are differences in the reactivity of the various reactive hydroxyl groups in these compounds and that these differences can be utilized to prepare desirable new derivatives.

The present invention provides new etherified anthracycline glycoside derivatives having the general formula

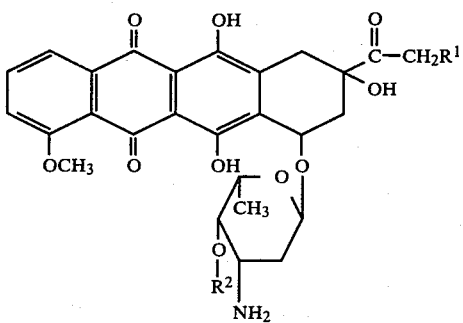

wherein $R^1$ represents hydrogen, hydroxyl, tetrahydropyranyloxy, $C_2$–$C_7$ alkanoyloxy or phenylacetyloxy and $R^2$ represents hydrogen, $C_1$–$C_8$ alkyloxyethyl, cyclohexyloxyethyl, tetrahydrofuranyl, tetrahydropyranyl, 6-methoxytetrahydropyranyl, 6-carbomethoxytetrahydropyranyl or 6-acetoxymethyltetrahydropyranyl, with the provisos that (1) when $R^1$ is hydrogen or hydroxyl, $R^2$ is not hydrogen and (2) when $R^1$ is tetrahydropyranyloxy, $R^2$ is hydrogen or tetrahydropyranyl, and nontoxic acid addition salts thereof.

A preferred embodiment of the invention comprises etherified anthracycline glycoside derivatives of the formula

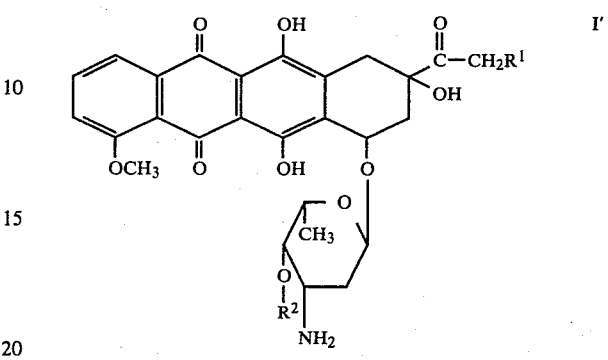

wherein $R^1$ represents a hydrogen atom, a hydroxyl group or a tetrahydropyranyloxy group and $R^2$ represents a hydrogen atom or a tetrahydropyranyl group, providing that when $R^1$ is a hydrogen atom or a hydroxyl group, $R^2$ is a tetrahydropyranyl group, and nontoxic acid addition salts thereof. Within the compounds of formula I', especially preferred are derivatives wherein (1) $R^1$ is hydrogen and $R^2$ is tetrahydropyranyl;
(2) $R^1$ is tetrahydropyranyloxy and $R^2$ is hydrogen;
(3) $R^1$ is tetrahydropyranyloxy and $R^2$ is tetrahydropyranyl; and
(4) $R^1$ is hydroxyl and $R^2$ is tetrahydropyranyl.

Another preferred embodiment of the invention comprises etherified anthracycline glycoside derivatives of the formula

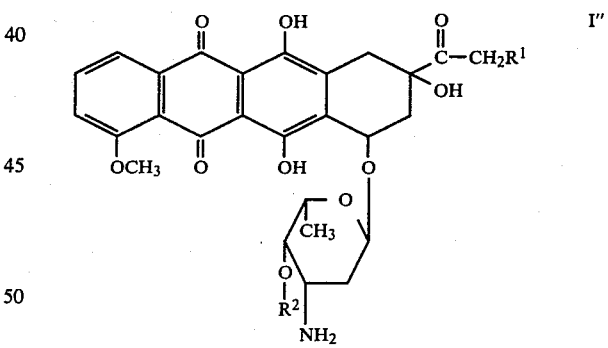

wherein $R^1$ is a hydrogen atom, a hydroxyl group, an alkanoyloxy group having from 2 to 7 carbon atoms inclusive or a phenylacetyloxy group and $R^2$ is alkyloxyethyl in which the alkyl portion has from 1 to 8 carbon atoms inclusive, cyclohexyloxyethyl, tetrahydrofuranyl, tetrahydropyranyl, 6-methoxytetrahydropyranyl, 6-carbomethoxytetrahydropyranyl or 6-acetoxymethyltetrahydropyranyl, with the proviso that when $R^1$ is hydrogen or hydroxyl, $R^2$ is not tetrahydropyranyl, and nontoxic acid addition salts thereof. Within the compounds of formula I'', especially preferred are derivatives wherein (1) $R^1$ is acetyloxy, isobutyloyloxy or phenylacetyloxy and $R^2$ is $C_1$–$C_8$ alkyloxyethyl, cyclohexyloxyethyl, tetrahydrofuranyl, tetrahydropyranyl, 6- methoxytetrahydropyranyl, 6-carbomethoxytetrahydropyranyl or 6-acetoxymethyltetrahydropyranyl, (2) $R^1$ is hydrogen or hydroxyl and $R^2$ is $C_1$-$C_8$ alkyloxyethyl, cyclohexyloxyethyl, tetrahydrofuranyl, 6-methoxytetrahydropyranyl, 6-carbomethoxytetrahydropyranyl or 6-acetoxymethyltetrahydropyranyl;

(3) $R^1$ is phenylacetyloxy or $C_2$-$C_7$ alkanoyloxy and $R^2$ is $C_1$-$C_8$ alkyloxyethyl, cyclohexyloxyethyl, tetrahydrofuranyl, tetrahydropyranyl, 6-methoxytetrahydropyranyl, 6-carbomethoxytetrahydropyranyl or 6-acetoxymethyltetrahydropyranyl;

(4) $R^1$ is hydroxyl and $R^2$ is $C_1$-$C_8$ alkyloxyethyl, cyclohexyloxyethyl, tetrahydrofuranyl, 6-methoxytetrahydropyranyl, 6-carbomethoxytetrahydropyranyl or 6-acetoxymethyltetrahydropyranyl; and (5) $R^1$ is hydrogen and $R^2$ is $C_1$-$C_8$ alkyloxyethyl, cyclohexyloxyethyl, tetrahydrofuranyl, 6-methoxytetrahydropyranyl, 6-carbomethoxytetrahydropyranyl or 6-acetoxymethyltetrahydropyranyl.

Specific examples of etherified derivatives provided by the present invention include:

4'-O-tetrahydropyranyl daunomycin (isomers a and b);
4',14-bis(O-tetrahydropyranyl)adriamycin (isomers a and b);
4'-O-tetrahydropyranyl adriamycin (isomers a and b);
14-O-tetrahydropyranyl adriamycin;
14-O-acetyl-4'-O-tetrahydropyranyl adriamycin (isomers a and b);
14-O-isobutyloyl-4'-O-tetrahydropyranyl adriamycin (isomers a and b);
14-O-phenylacetyl-4'-O-tetrahydropyranyl adriamycin (isomers a and b);
14-O-phenylacetyl-4'-O-(6-methoxytetrahydropyranyl)adriamycin (isomers a and b);
14-O-phenylacetyl-4'-O-(6-carbomethoxytetrahydropyranyl)adriamycin (isomers a and b);
14-O-isobutyloyl-4'-O-(6-acetoxytetrahydropyranyl)adriamycin (isomers a and b);
14-O-acetyl-4'-O-tetrahydrofuranyl adriamycin (isomers a and b);
14-O-isobutyloyl-4'-O-tetrahydrofuranyl adriamycin (isomers a and b);
14-O-phenylacetyl-4'-O-tetrahydrofuranyl adriamycin (isomers a and b);
14-O-phenylacetyl-4'-O-(1-ethyloxyethyl)adriamycin (isomers a and b);
14-O-acetyl-4'-O-(1-butyloxyethyl)adriamycin (isomers a and b);
14-O-acetyl-4'-O-(1-isobutyloxyethyl)adriamycin (isomers a and b);
14-O-isobutyloyl-4'-O-(1-isobutyloxyethyl)adriamycin (isomers a and b);
14-O-phenylacetyl-4'-O-(1-isobutyloxyethyl)adriamycin (isomers a and b);
14-O-acetyl-4'-O-(1-(6-methylheptyloxy)ethyl)adriamycin (isomers a and b);
14-O-acetyl-4'-O-cyclohexyloxyethyl adriamycin (isomers a and b);
4'-O-tetrahydrofuranyl adriamycin;
4'-O-tetrahydrofuranyl adriamycin (isomers a and b);
4'-O-(1-ethyloxyethyl)adriamycin (isomers a and b);
4'-O-(1-butyloxyethyl)adriamycin (isomers a and b);
4'-O-(1-isobutyloxyethyl)adriamycin (isomers a and b);
4'-O-(1-(6-methylheptyloxy)ethyl)adriamycin (isomers a and b);
4'-O-cyclohexyloxyethyl adriamycin (isomers a and b);
4'-O-(6-methoxytetrahydropyranyl)adriamycin (isomers a and b);
4'-O-(6-carbomethoxytetrahydropyranyl)adriamycin (isomers a and b);
4'-O-(6-acetoxytetrahydropyranyl)adriamycin (isomers a and b);
4'-O-tetrahydrofuranyl daunomycin (isomers a and b);
4'-O-(1-ethyloxyethyl)daunomycin (isomers a and b);
4'-O-(1-butyloxyethyl)daunomycin (isomers a and b);
4'-O-(1-isobutyloxyethyl)daunomycin (isomers a and b);
4'-O-(1-(6-methylheptyloxy)ethyl)daunomycin (isomers a and b);
4'-O-cyclohexyloxyethyl daunomycin (isomers a and b);
4'-O-(6-methoxytetrahydropyranyl)daunomycin (isomers a and b);
4'-O-(6-carbomethoxytetrahydropyranyl)daunomycin (isomers a and b);
4'-O-(6-acetoxytetrahydropyranyl)daunomycin (isomers a and b).

In one aspect of the present invention (hereinafter referred to as Process 1), tetrahydropyranyl ether derivatives of the formula

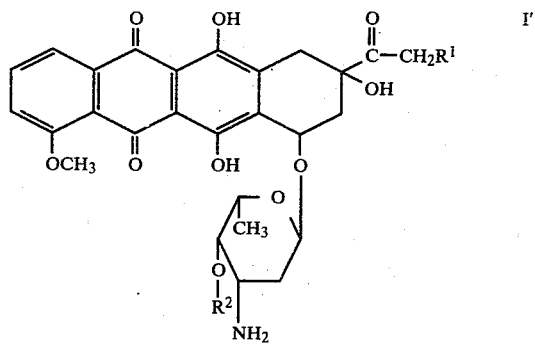

wherein $R^1$ represents a hydrogen atom, a hydroxyl group or a tetrahydropyranyloxy group and $R^2$ represents a hydrogen atom or a tetrahydropyranyl group, with the proviso that when $R^1$ is a hydrogen atom or hydroxyl group, $R^2$ is a tetrahydropyranyl group, and nontoxic acid addition salts thereof, are prepared by reacting the free base of adriamycin or daunomycin or an acid addition salt therof (e.g. the hydrochloride) in an inert organic solvent with 3,4-dihydro-2H-pyran (dihydropyran) in the presence of an acid catalyst to convert one or both of the hydroxyl groups at C-4' or C-14 to tetrahydropyranyloxy groups and, if desired, selectively converting the C-14 tetrahydropyranyloxy group of a di-tetrahydropyranyl product to a hydroxyl group by alcoholysis or hydrolysis and, if desired, carrying out one or more of the further steps selected from (a) converting by methods known per se a product in the form of the free base or acid addition salt thereof to a nontoxic acid addition salt thereof or (b) converting by methods known per se a product in the form of an acid addition salt to the corresponding free base product.

The general reaction processes for preparing the compounds of formula I' may be more easily seen from the following schemes:

Scheme I

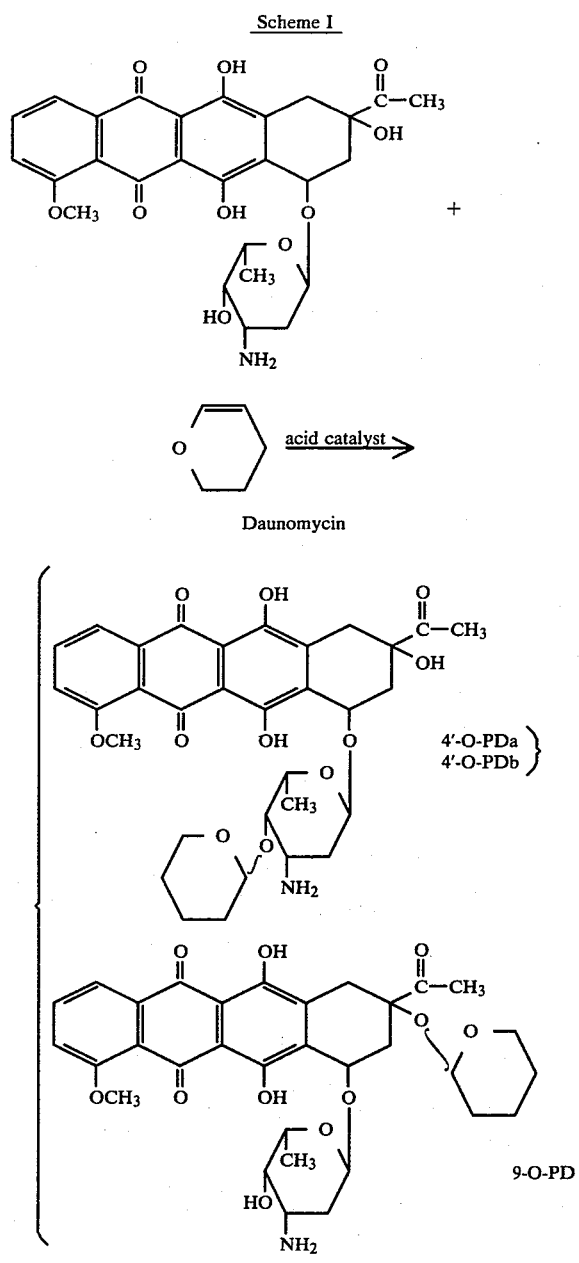

Scheme II

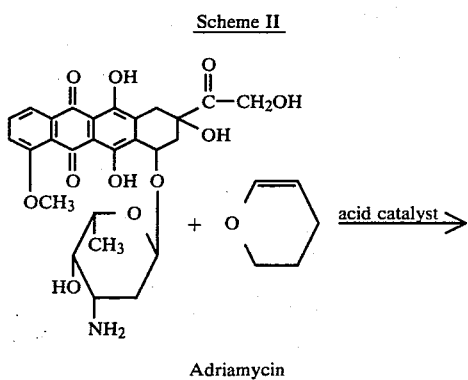

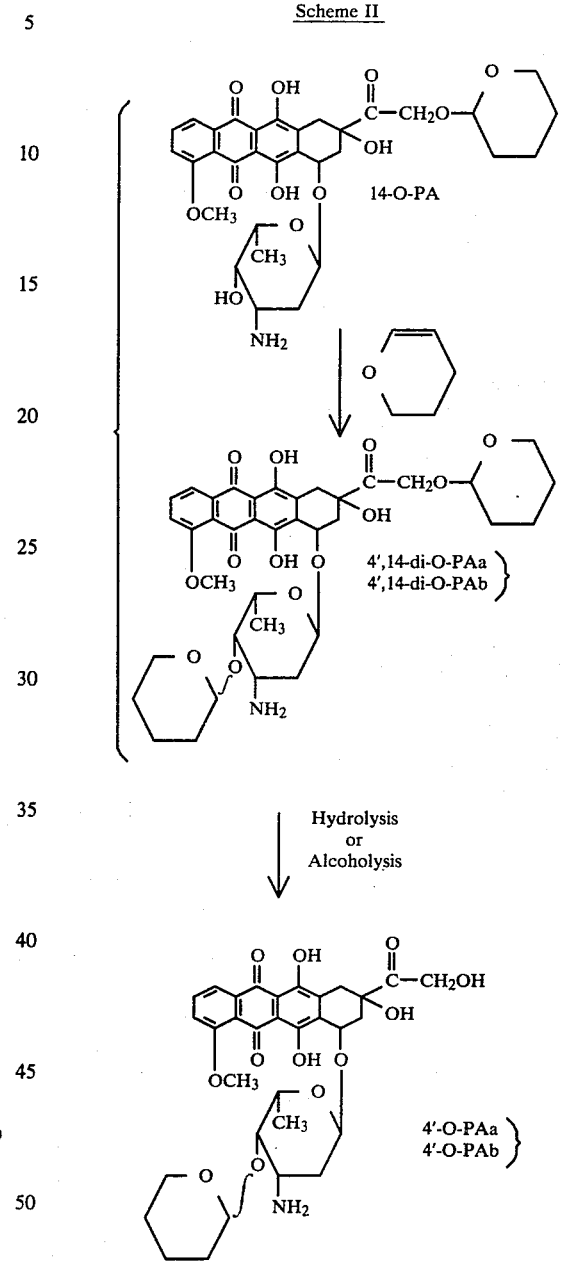

The particular reaction products formed, the ratios of the different products and the reaction yields vary with the reaction conditions used, e.g. solvent, acid catalyst, ratio of reactants, temperature, reaction time, etc.

In another aspect of the present invention (hereinafter referred to as Process 2A), anthracycline glycoside derivatives of the formula

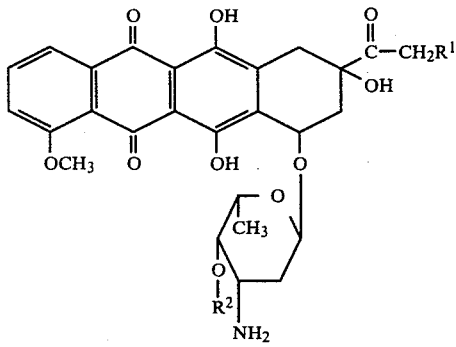

wherein $R^1$ is hydroxyl, $C_2$–$C_7$ alkanoyloxy or phenylacetyloxy and $R^2$ is $C_1$–$C_8$ alkyloxyethyl, cyclohexyloxyethyl, tetrahydrofuranyl, tetrahydropyranyl, 6-methoxytetrahydropyranyl, 6-carbomethoxytetrahydropyranyl or 6-acetoxymethyltetrahydropyranyl, or nontoxic acid addition salts thereof, may be prepared by etherifying the C-4' hydroxyl group of an anthracycline derivative of the formula

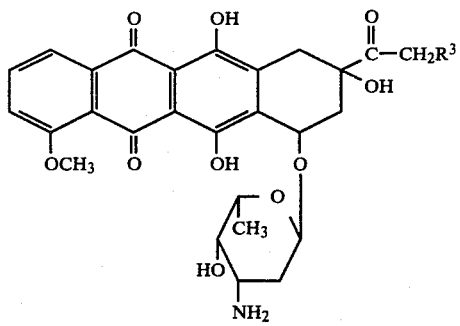

wherein $R^3$ is $C_2$–$C_7$ alkanoyloxy or phenylacetyloxy, or an acid addition salt thereof, with dihydrofuran, dihydropyran, 2-acetoxyethyl-3,4-dihydro-2H-pyran, 2-methoxy-3,4-dihydro-2H-pyran, 2-carbomethoxy-3,4-dihydro-2H-pyran or an alkyl vinyl ether of the formula $CH_2{=}CHOR^5$ in which $R^5$ is $C_1$–$C_8$ alkyl (straight or branched chain) or cyclohexyl in an inert organic solvent and in the presence of an acid catalyst to produce a C-4' etherified derivative of the formula

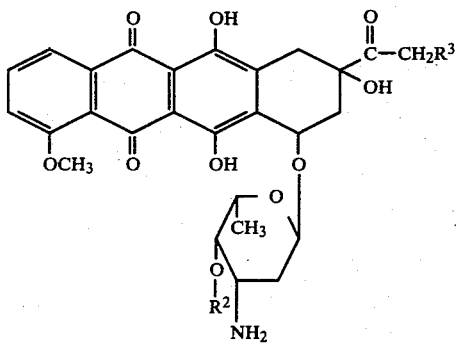

, or an acid addition salt thereof, and, if desired, carrying out one or more of the further steps selected from (a) eliminating the alkanoyl group or phenylacetyl group at the C-14 position of compound III by hydrolytic deacylation to produce an anthracycline derivative of the formula

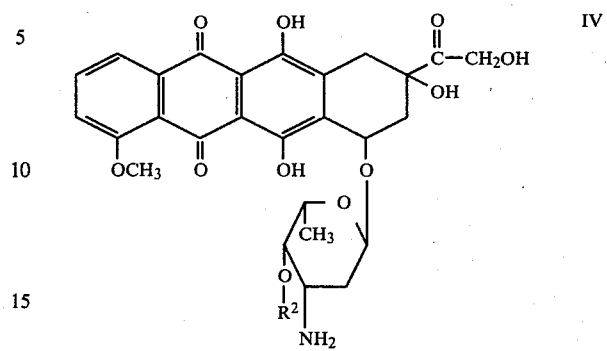

, or an acid addition salt thereof, (b) converting by methods known per se a product in the form of the free base or acid addition salt thereof to a nontoxic acid addition salt thereof, or (c) converting by methods known per se a product in the form of an acid addition salt to the corresponding free base product.

In still another aspect of the present invention (hereinafter referred to as Process 2B), anthracycline glycoside derivatives of the formula

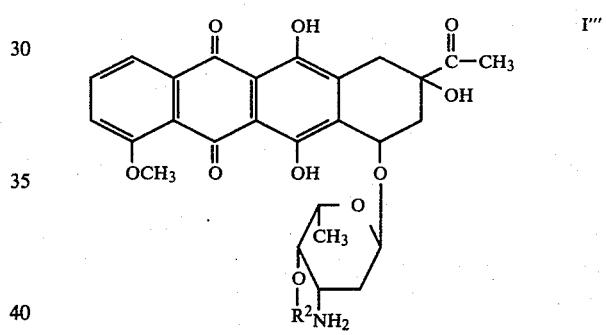

wherein $R^2$ is $C_1$–$C_8$ alkyloxyethyl, cyclohexyloxyethyl, tetrahydrofuranyl, 6-methoxytetrahydropyranyl, 6-carbomethoxytetrahydropyranyl or 6-acetoxymethyltetrahydropyranyl, or nontoxic acid addition salts thereof, may be prepared by etherifying the C-4' hydroxyl group of daunomycin, or an acid addition salt thereof, with dihydrofuran, 2-acetoxyethyl-3,4-dihydro-2H-pyran, 2-methoxy-3,4-dihydro-2H-pyran, 2-carbomethoxy-3,4-dihydro-2H-pyran or an alkyl vinyl ether of the formula $CH_2{=}CHOR^5$ in which $R^5$ is $C_1$–$C_8$ alkyl or cyclohexyl in an inert organic solvent and in the presence of an acid catalyst and, if desired, carrying out one or more of the further steps selected from (a) converting by methods known per se a product in the form of the free base or acid addition salt thereof to a nontoxic acid addition salt thereof, or (b) converting by methods known per se a product in the form of an acid addition salt to the corresponding free base product.

The starting material glycosides employed in the above-described etherification processes can be in free base form or in the form of an acid addition salt. Since acid addition salts of the etherified products may be converted by known methods to the corresponding free base products or to nontoxic acid addition salts, it is not necessary for a starting material salt to be nontoxic.

Any nonreactive organic solvent may be used for the etherification reactions. Examples of suitable solvents include benzene, toluene, xylene, dimethylformamide, acetonitrile, tetrahydrofuran, dimethylsulfoxide and dioxane. The reaction solvent is preferably anhydrous and can be a single solvent or mixture of solvents. A most preferred solvent is anhydrous dimethylformamide.

The acid catalyst used in the above reactions may be any organic (e.g. formic, trifluoroacetic) or inorganic (e.g. hydrochloric, phosphoric) acid. A preferred class of acid catalysts comprises the organic sulfonic acids. More preferred catalysts are the aromatic sulfonic acids such as p-toluenesulfonic acid and benzene-sulfonic acid. A most preferred catalyst is p-toluenesulfonic acid.

The etherification reaction temperature is not critical. Good results have been achieved at room temperature, although temperatures higher or lower than this may also be used.

Reaction time will vary with the particular process conditions selected, e.g. temperature, catalyst, solvent, etc. Selection of optimum reaction time to produce a specific product or mixture of products may be made by routine experimentation using the thin layer assays described below and in the examples. As an example etherification may be carried out for 20 minutes to 50 hours at room temperature using p-toluenesulfonic acid as an acid catalyst and solvents such as anhydrous dimethylformamide, anhydrous dimethylsulfoxide and anhydrous tetrahydrofuran or anhydrous dioxane and anhydrous dimethylsulfoxide.

As mentioned above in connection with Process 1, the particular reaction products and reaction yield are dependent on such factors as the concentration of starting materials and ratios of reactants. When using daunomycin as a starting material, the principal products are 4'-O-tetetrahydropyranyl daunomycin (abbreviated as 4'-O-PD) and 9-O-tetrahydropyranyl daunomycin (abbreviated as 9-O-PD). These products may be detected in the reaction mixture by silica gel thin layer chromatography (Merck Co. 60 $F_{254}$) using a mixture of chloroform-methanol-acetic acid (80:20:4 v/v) as a developer. The products appear at $R_f$ 0.74 (4'-O-PD) and $R_f$ 0.15 (9-O-PD). The product 4'-O-PD was separated into two components having $R_f$ values of 0.46 and 0.65 on silica gel TLC chromatography using a mixture of chloroform-methanol (10:1 v/v). These components were found be diastereomers of 4'-O-PD. Components $R_f$ 0.46 and $R_f$ 0.65 were arbitrarily designated as 4'-O-PDa (isomer A) and 4'-O-PDb (isomer b), respectively. When using adriamycin as the starting material in Process 1, the main products detected using the above-mentioned silica gel TLC procedure were 14-O-tetrahydropyranyl adriamycin (14-O-PA) having $R_f$=0.12 and two components which are diastereomers of 4', 14-di(O-tetrahydropyranyl)adriamycin, i.e. 4', 14-di(O-tetrahydropyranyl)adriamycin (isomer a), abbreviated 4', 14-di-O-PAa at $R_f$ 0.55 and 4', 14-di(O-tetrahydropyranyl)adriamycin (isomer b), abbreviated 4',14-di-O-PAb at $R_f$ 0.73. The compound 4',14-di(O-tetrahydropyranyl)adriamycin may also be named 4',14-bis-(O-tetrahydropyranyl)adriamycin.

The diasteromeric mixture of 4',14-di-O-PAa and 4',14-di-O-PAb obtained in Process 1 may also be prepared in high yield by etherifying 14-O-tetrahydropyranyl adriamycin or an acid addition salt thereof with 3,4-dihydro-2H-pyran in an inert organic solvent and in the presence of an acid catalyst.

By utilizing the difference in reactivity between the C-14 primary hydroxyl group and the C-4' secondary hydroxyl group, the tetrahydropyranyl group at C-14 of 4',14-di-O-PAa and 4',14-di-O-PAb (or an acid addition salt thereof) can be selectively removed by hydrolysis or alcoholysis to produce in good yield the corresponding diastereomers of 4'-O-PAa and 4'-O-PAb. Conversion of the tetrahydropyranyloxy group to a hydroxy group may be carried out for example by hydrolysis with acidified water (i.e. aqueous inorganic or organic acid) or by alcoholysis with an alcohol or phenol (e.g. a $C_1$–$C_6$ alkanol). A convenient procedure comprises treatment with dilute acetic acid solution or p-toluenesulfonic acid-methanol solution at room temperature for a period of from about 30 minutes to 5 hours. Side reactions can be minimized by carrying out the hydrolysis or alcoholysis reaction in the dark.

To eliminate the acyl group or phenylacyl group at the C-14 position in Process 2A, a conventional hydrolysis procedure may be used. Thus, the alkanoyloxy or phenylacetyloxy group $R^3$ in compound II may be hydrolyzed to a hydroxy group by dissolving or suspending compound II in a water-miscible organic solvent such as a lower alcohol (methanol, ethanol, etc.) or aqueous acetone at room temperature or with mild heating in the presence of base (e.g. $K_2CO_3$ at a concentration of about 10% w/v). Completion of the hydrolysis can be confirmed by thin-layer chromatography.

The etherified products of Processes 1, 2A and 2B may be isolated from the reaction mixture by conventional procedures. Thus, the etherified products may be recovered by neutralizing the reaction mixture with a basic substance (e.g. an alkali metal carbonate or bicarbonate), extracting the neutralized reaction mixture with a water-immiscible organic solvent (e.g. ethyl acetate, chloroform, methylene chloride, methyl isobutyl ketone, etc.), extracting the organic extract with dilute aqueous acid (organic or inorganic), neutralizing the aqueous acidic layer with a basic substance, extracting the neutralized aqueous layer with a water-immiscible organic solvent and concentrating the organic extract to dryness. The powder thus obtained may be purified by silica gel column chromatography or, in the case of a small sample, by preparative thin-layer chromatography. The products of the hydrolysis or alcoholysis reaction in Processes 1 and 2A may be recovered from the reaction mixture by neutralizing with a basic substance, extracting the neutralized reaction mixture with a water-immiscible organic solvent and concentrating the organic extract to dryness.

Products obtained in the form of a mixture of diastereomers (a and b isomers) may be separated by column or thin layer chromatography (using alumina, silica gel, etc.) into the individual a and b isomers in substantially pure form.

Products obtained in the above reaction procedures may be recovered in the form of the free base, an acid addition salt or a nontoxic acid addition salt. The free base products may be easily converted into nontoxic acid addition salts which are substantially equivalent in therapeutic activity to the corresponding free bases. The salts are formed, isolated, purified and formulated by the methods generally employed in salt formation for antibiotics, e.g. the anthracycline glycoside antibiotics. Thus, the free base may be reacted with a nontoxic acid in a suitable solvent and the salt recovered by lyophilization or by precipitation with an antisolvent, i.e. a solvent in which the desired salt is only slightly soluble. Products in the form of an acid addition salt may be converted to the corresponding free base by neutralization with a basic substance. Finally, toxic acid addition salts may be converted to nontoxic acid addition salts by neutralization and treatment with a non-toxic acid as described above.

Physicochemical Properties

Figure 2:
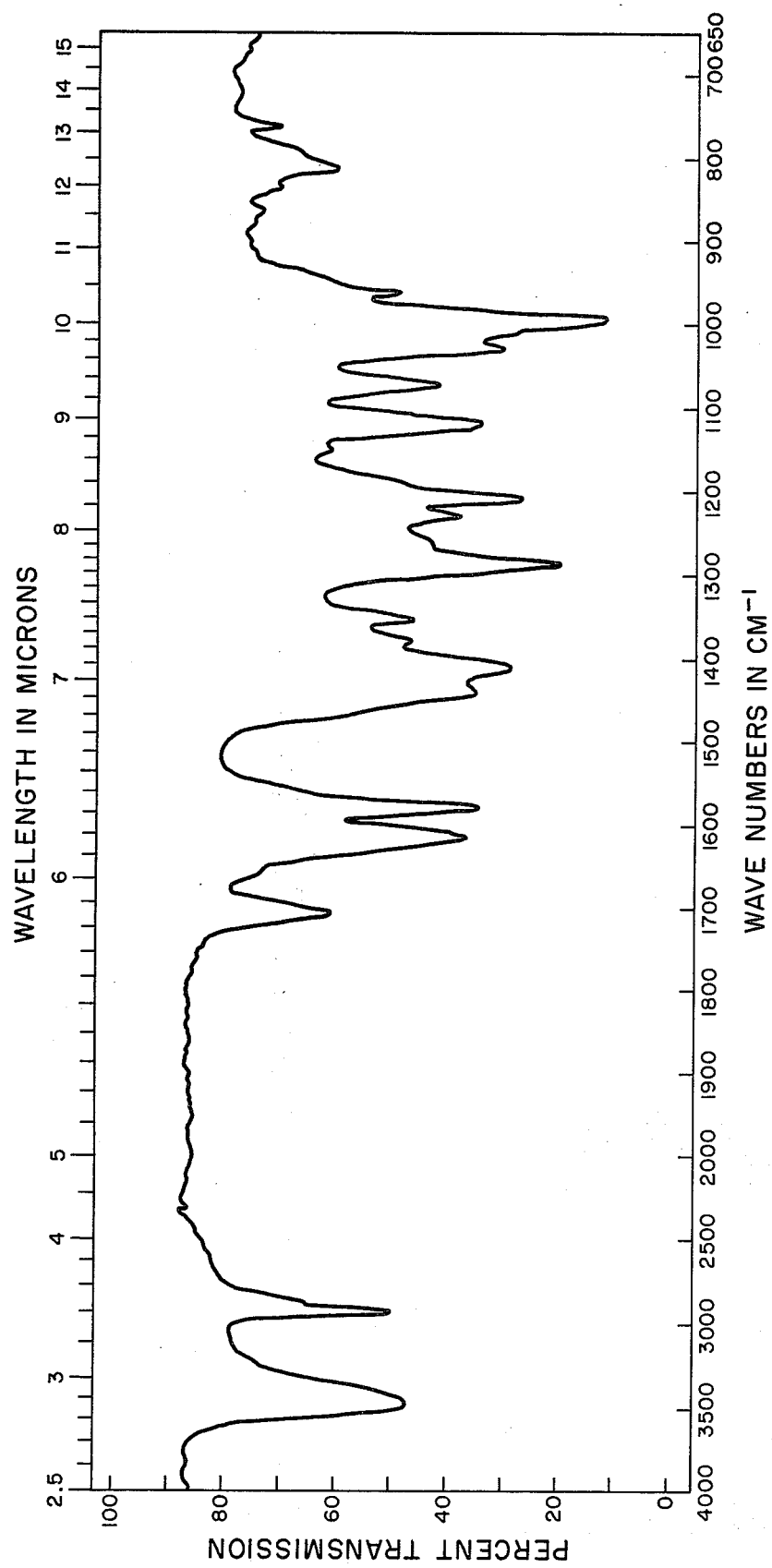
FIG. 2 shows the infrared absorption spectrum (KBr) of 4'-O-tetrahydropyranyl daunomycin (isomer b).
Figure 3:
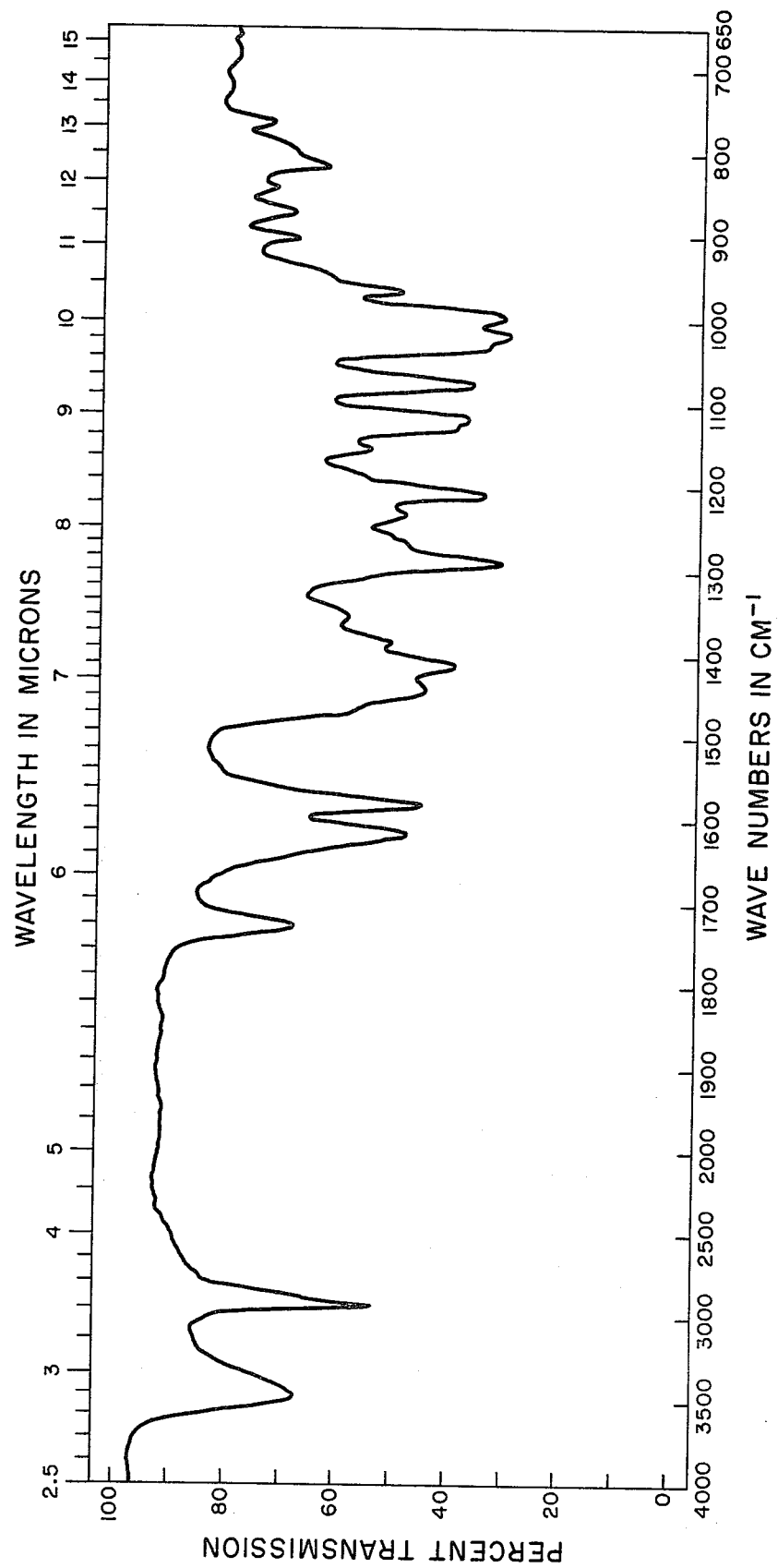
FIG. 3 shows the infrared absorption spectrum (KBr) of 4',14-bis(O-tetrahydropyranyl)adriamycin (isomer a).
Figure 4:
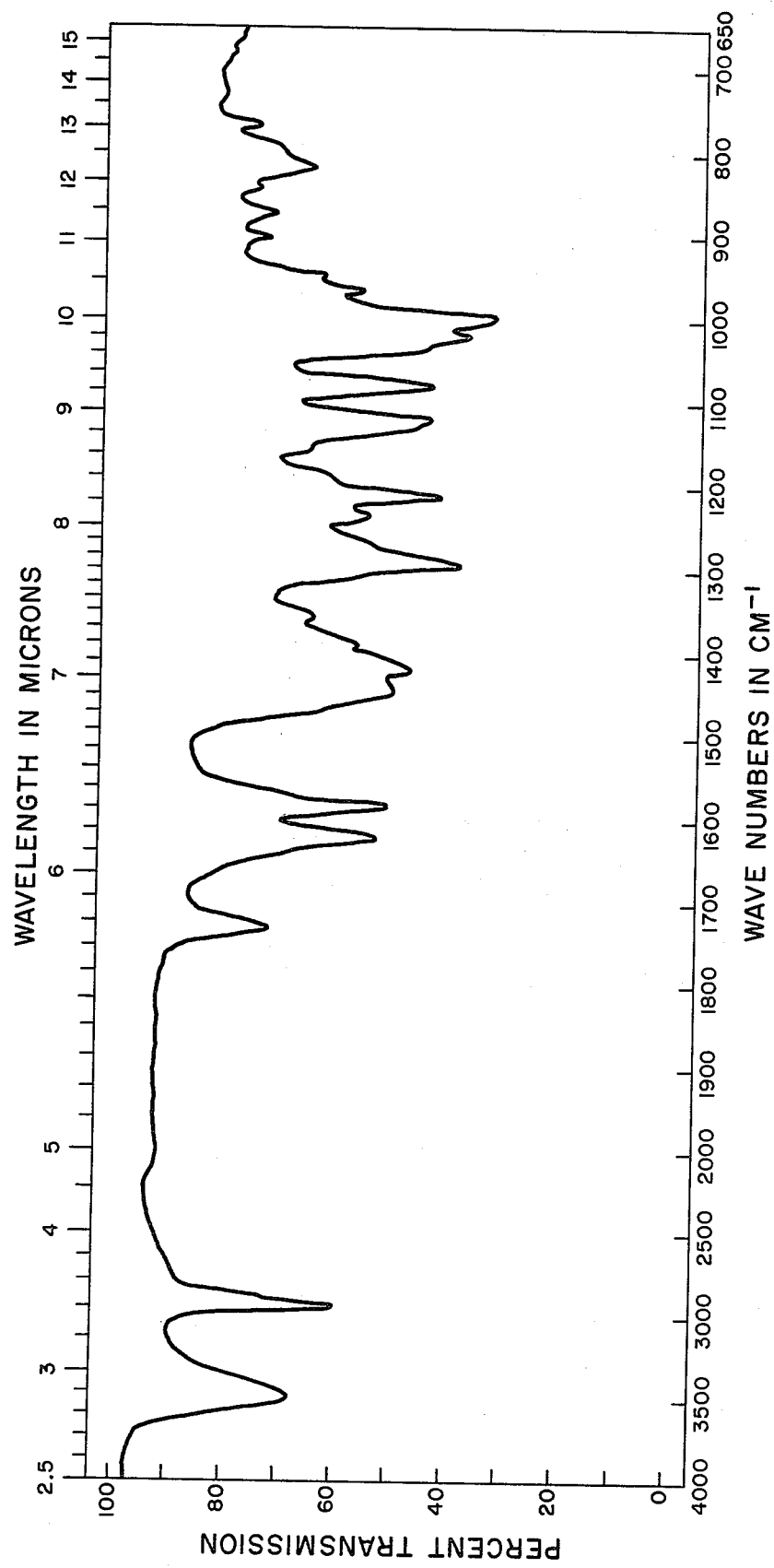
FIG. 4 shows the infrared absorption spectrum (KBr) of 4',14-bis(O-tetrahydropyranyl)adriamycin (isomer b).
Figure 5:
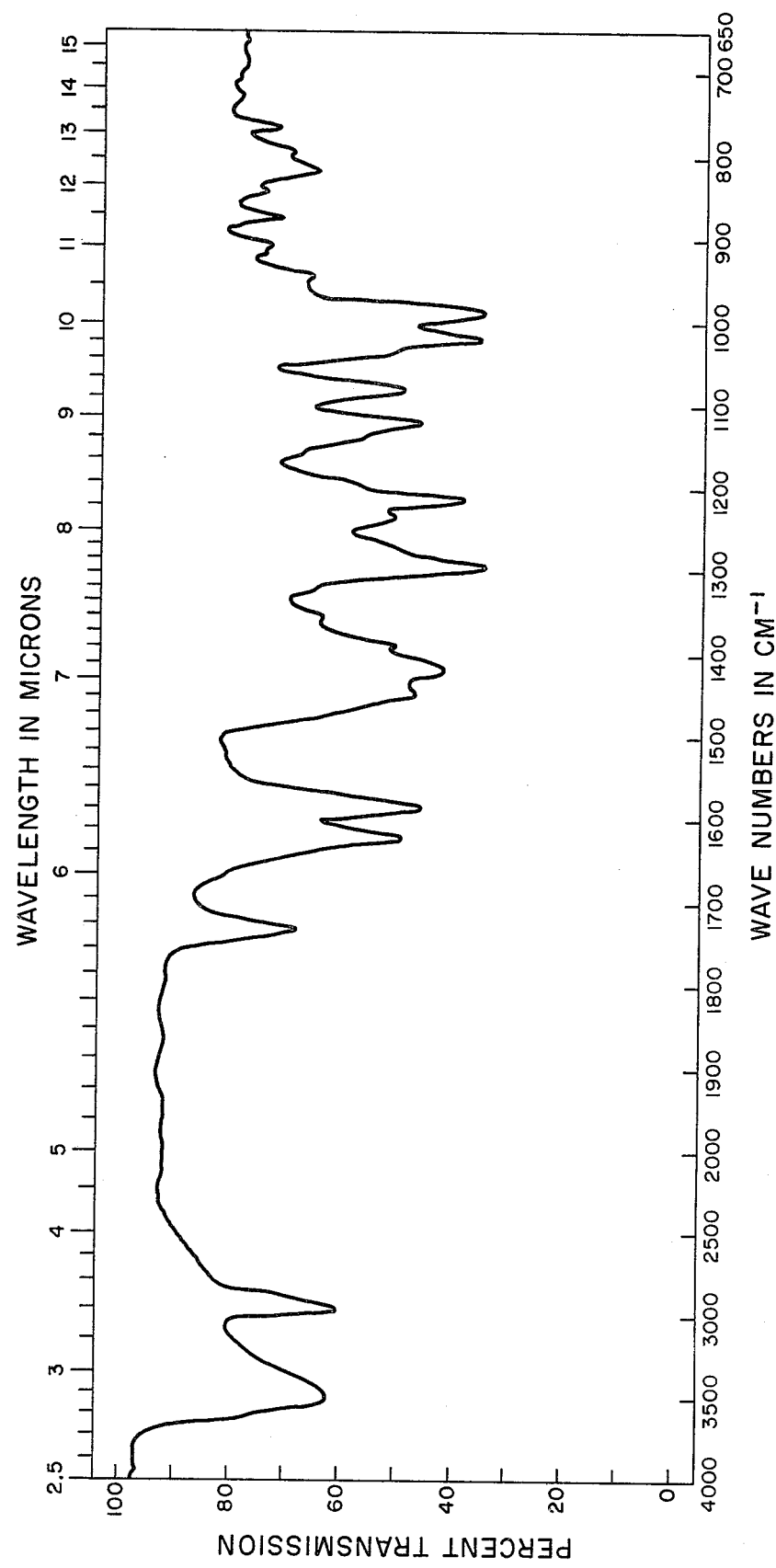
FIG. 5 shows the infrared absorption spectrum (KBr) of 14-O-tetrahydropyranyl adriamycin.
Figure 6:
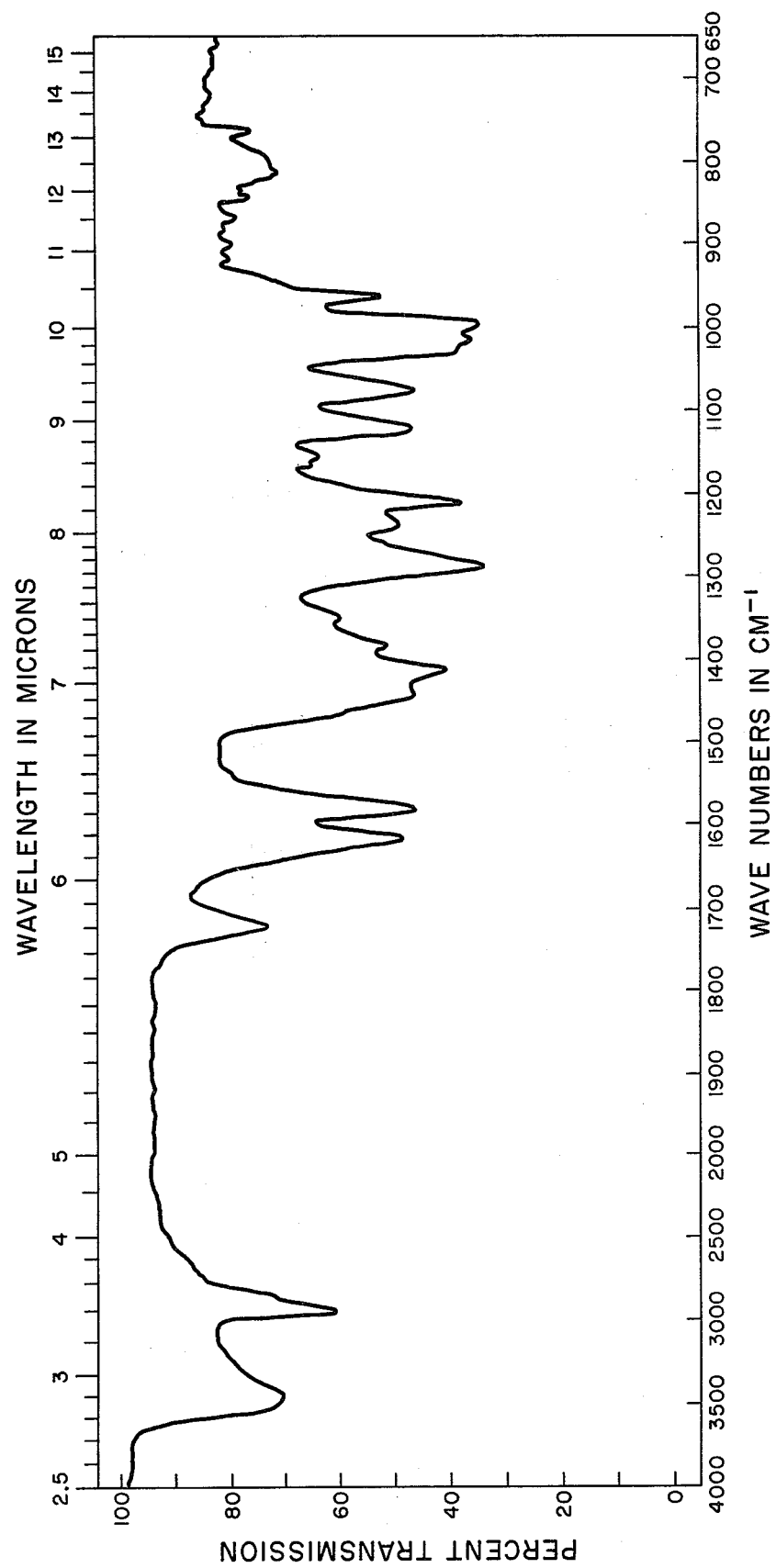
FIG. 6 shows the infrared absorption spectrum (KBr) of 4'-O-tetrahydropyranyl adriamycin (isomer a).
Figure 7:
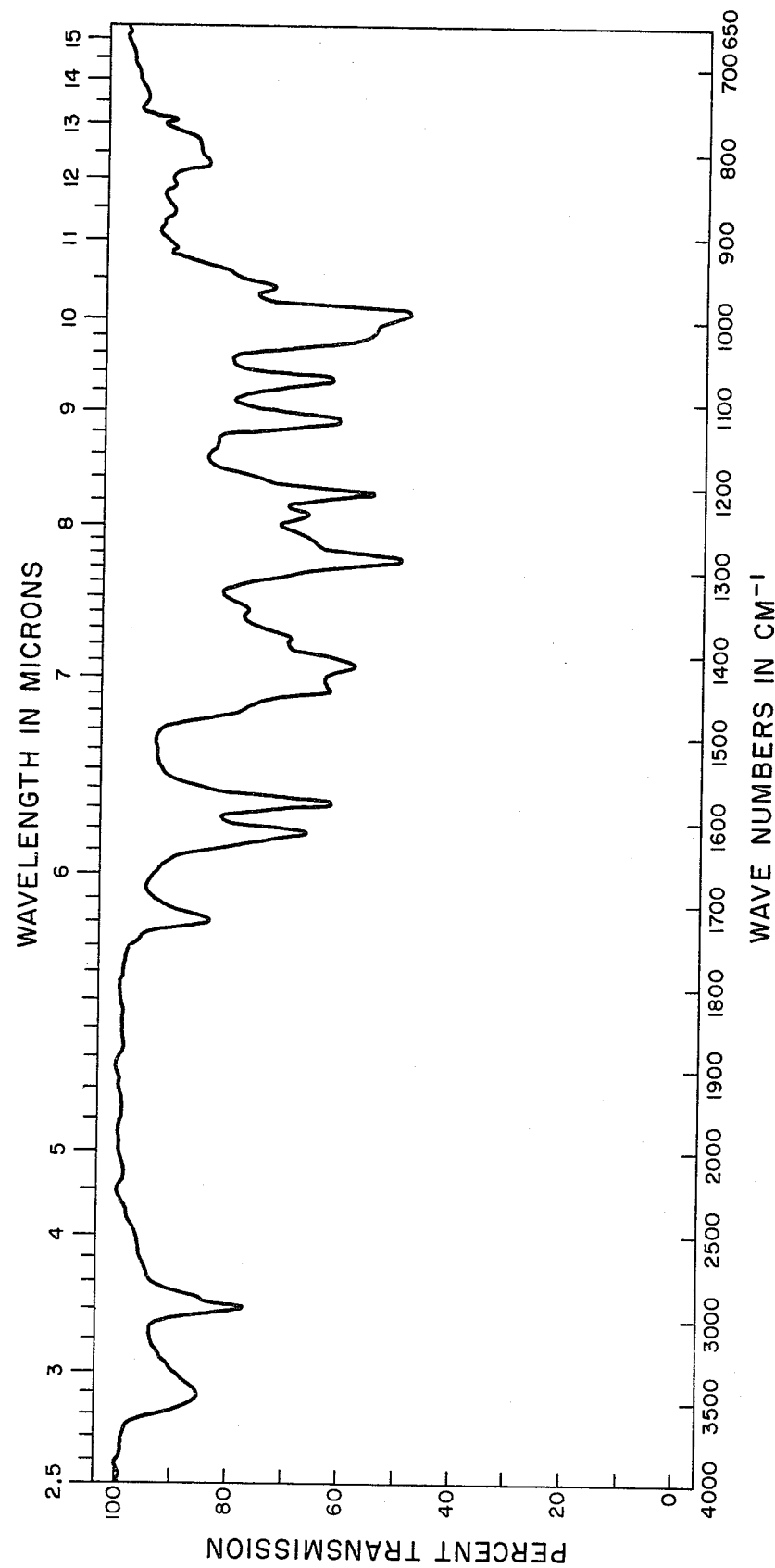
FIG. 7 shows the infrared absorption spectrum (KBr) of 4'-O-tetrahydropyranyl adriamycin (isomer b).
Figure 8:
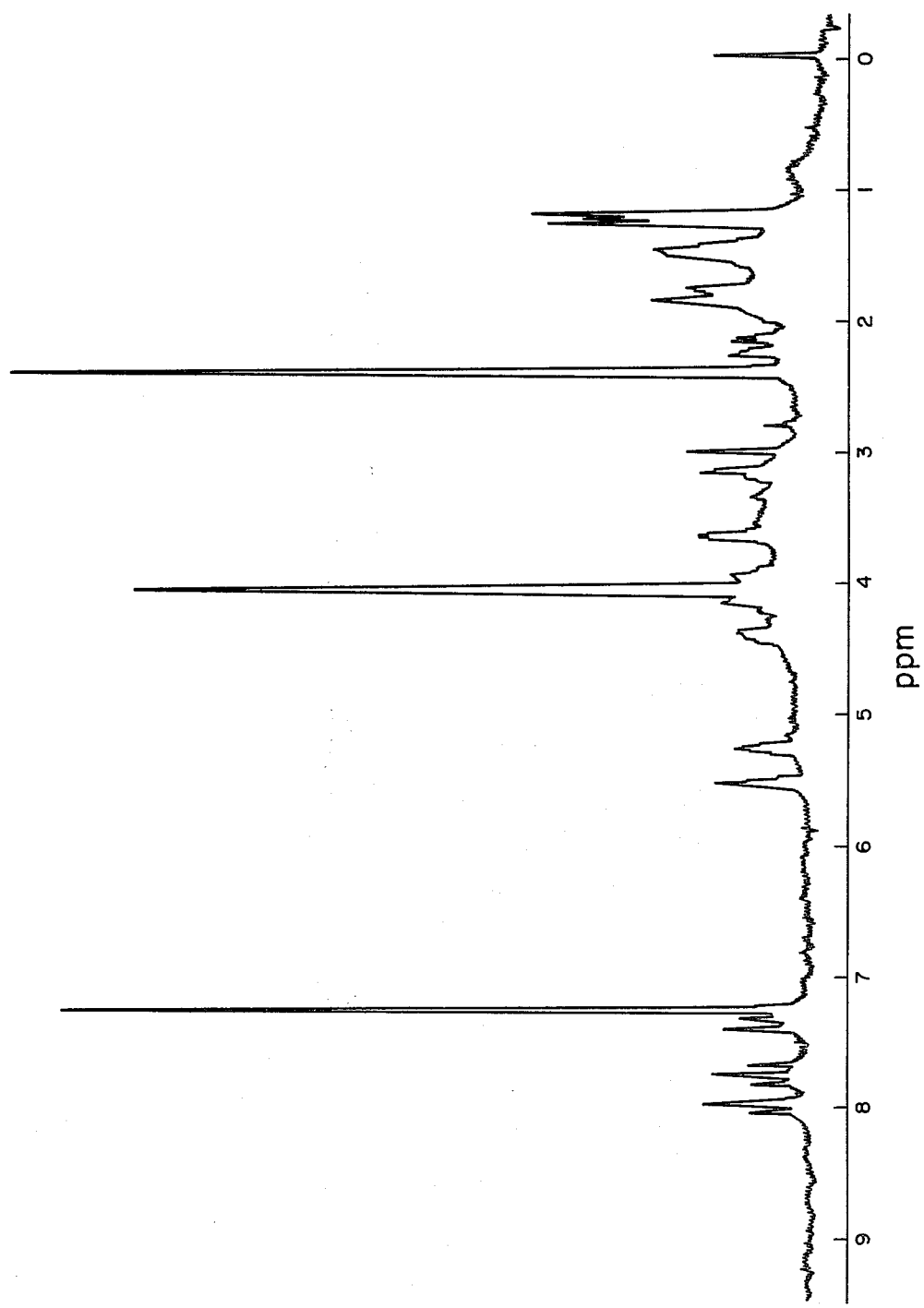
FIGS. 8 to 14 show proton NMR spectra (100 MHz, $CDCl_3$) of the compounds shown in the order of their infrared absorption spectra above.
Figure 9:
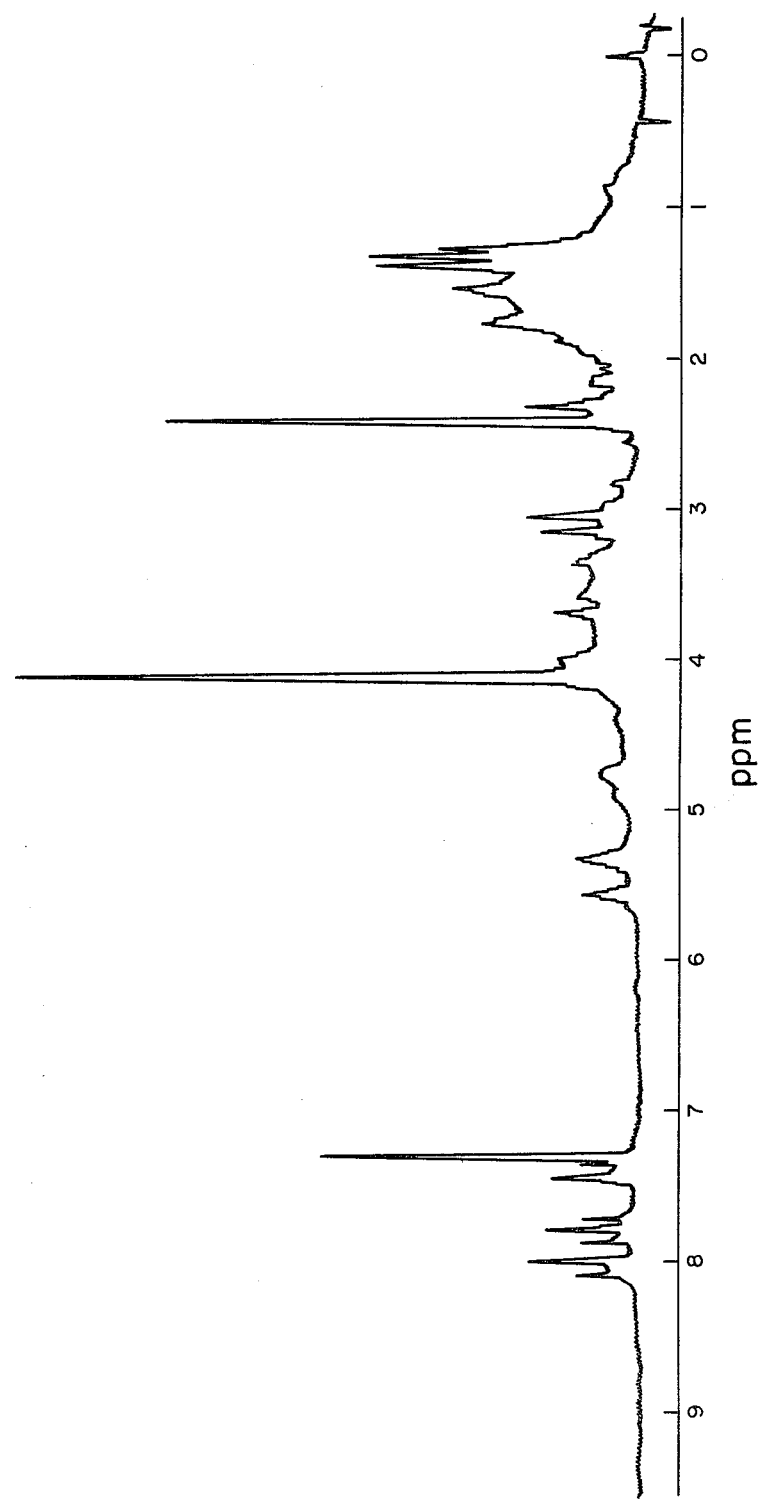
Figure 10:
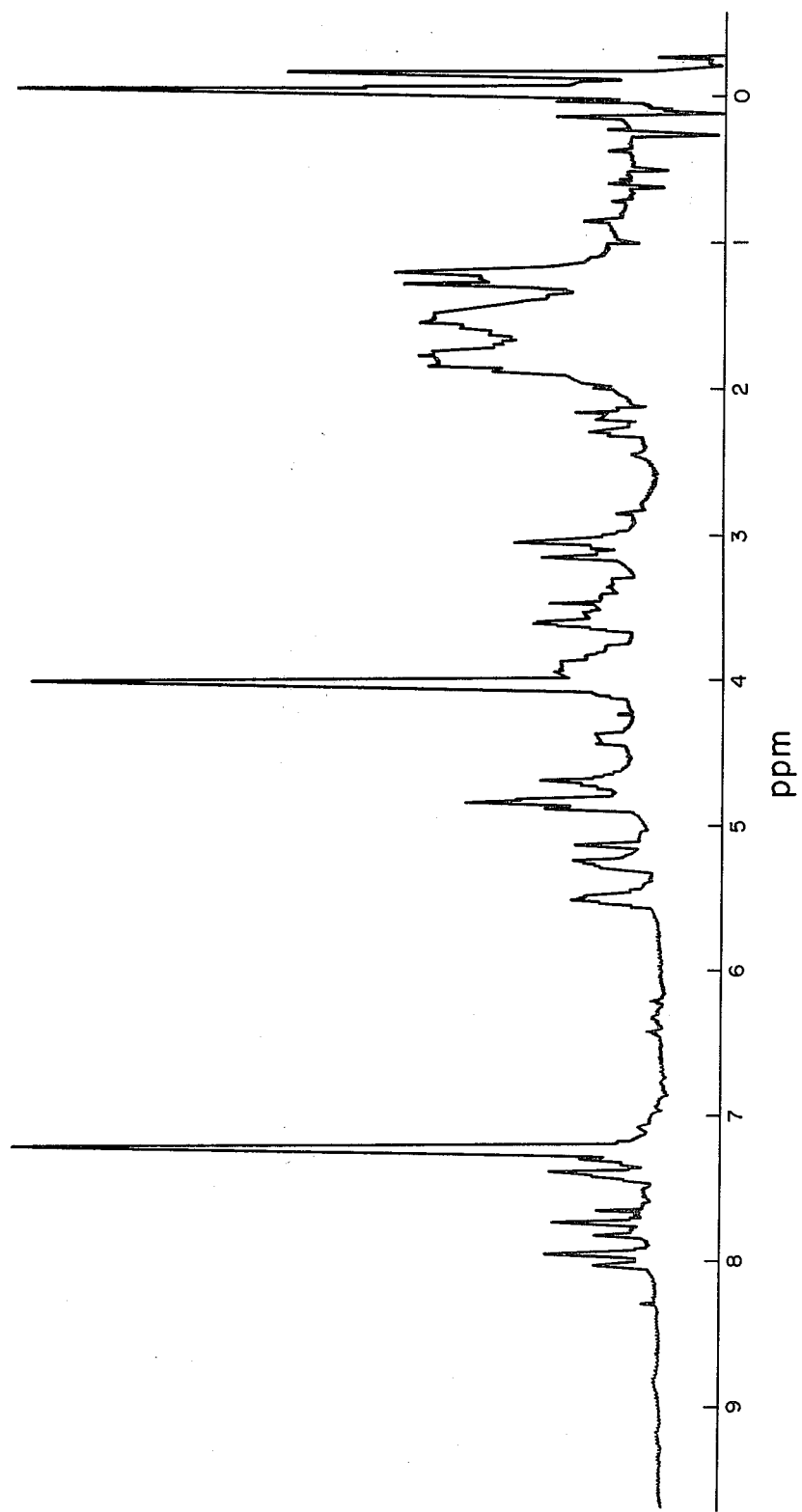
Figure 11:
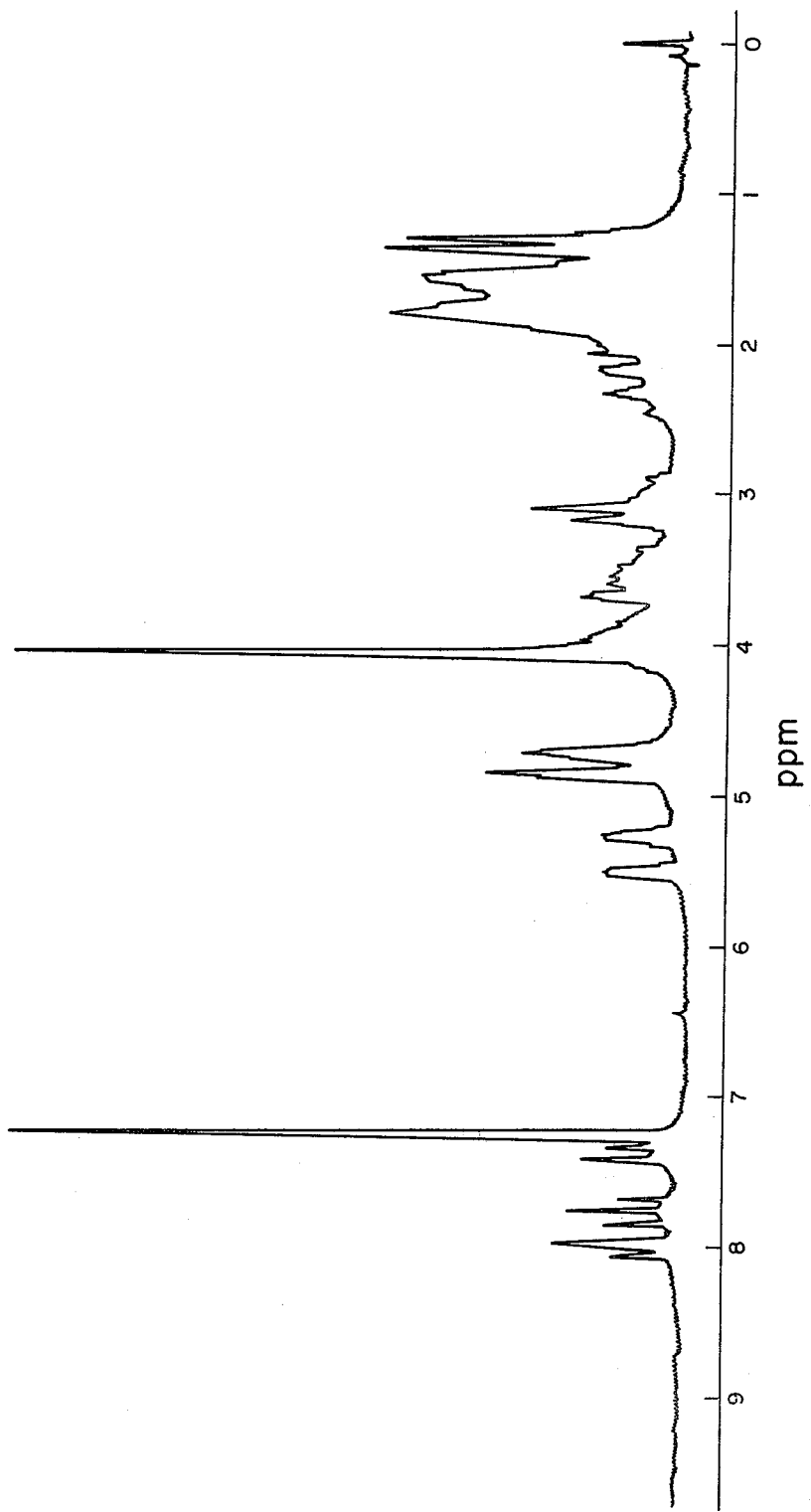
Figure 12:
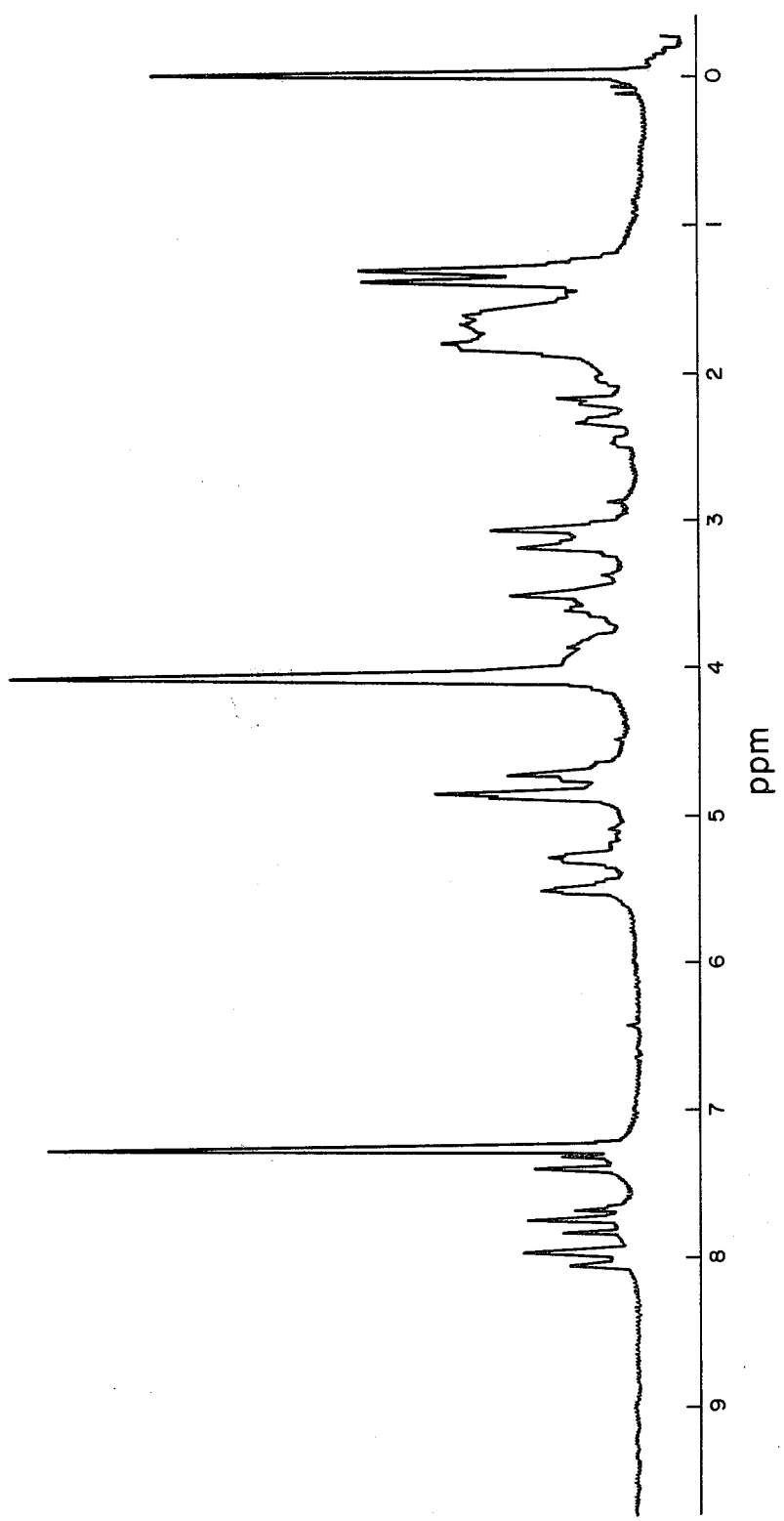
Figure 13:
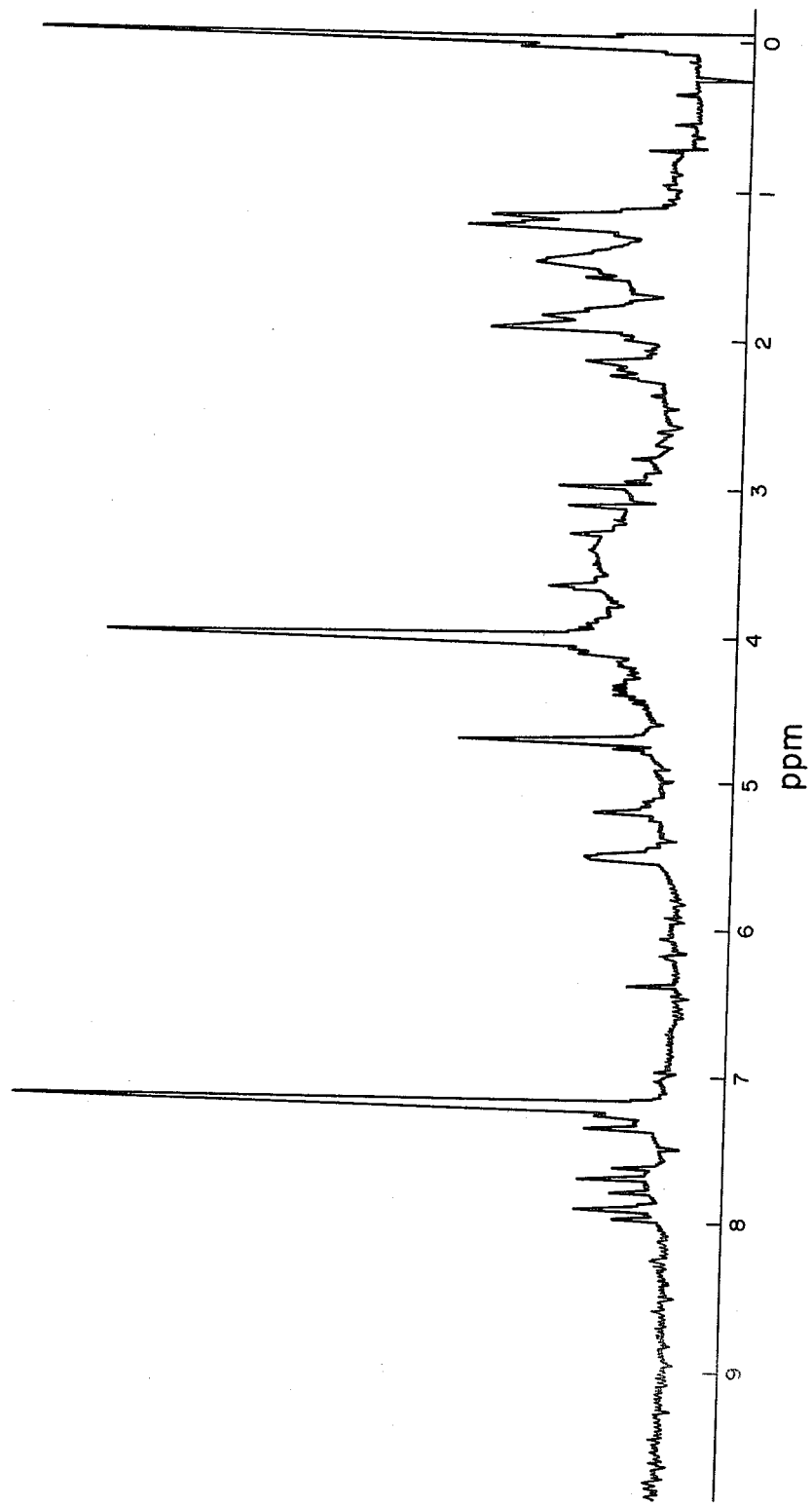
Figure 14:
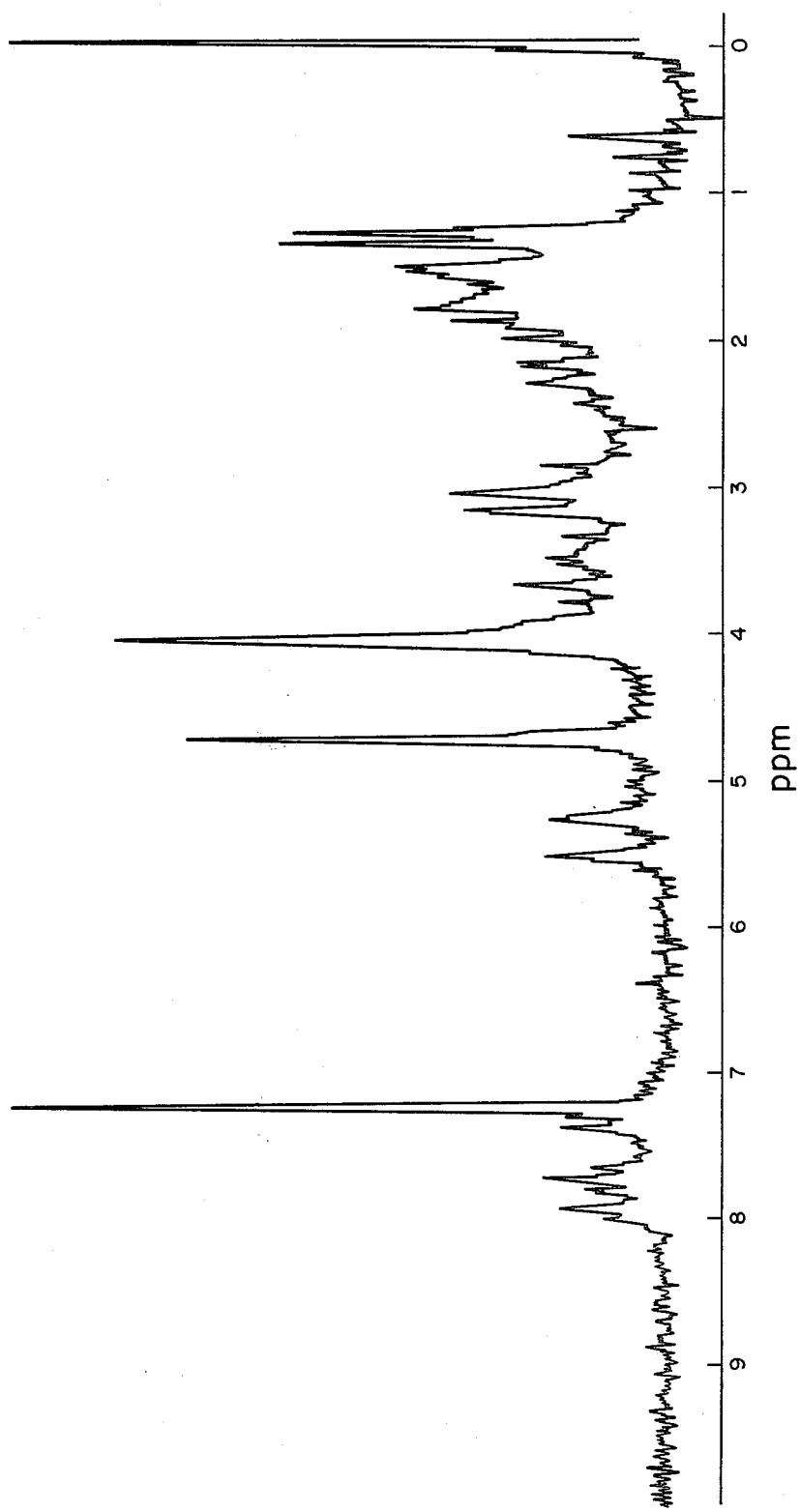

The compounds of general formula I' disclosed above exist in solid form as an amorphous or crystalline red powder. As free bases they are soluble in ethyl acetate, chloroform and ethanol and slightly soluble in water, n-hexane, petroleum ether, etc. Ethanol solutions and acidic solutions of the compounds are of a red color, give a positive ninhydrin reaction and do not reduce Fehling's solution. FIGS. 1–14 and Table 1 show the elemental analysis, melting point (decomposition), specific rotation (C=0.2 in CHCl$_3$), UV and visible absorption spectrum (methanol), infrared absorption spectrum (KBr tablet) and nuclear magnetic resonance spectrum (100 MHz, CDCl$_3$).

chemical shift of the C-4' proton in the daunosamine moiety towards a lower field (compared with that of daunomycin) due to the formation of the glycosidic bond at C-4'.

The difference in configuration between 4'-O-PDa and 4'-O-PDb, 4'-O-PAa and 4'-O-PAb and 4',14-di-O-PAa and 4',14-di-O-PAb is considered to be the difference in absolute configuration R and S at C-2 of the tetrahydropyranyl group since the chemical shifts and coupling constants (J value) at the C-2 and C-3 protons differ from each other. The absolute configuration, however, for the a and b isomers is still unknown. Table 2 shows the chemical shifts (from FIGS. 8–14) at C-2 of the tetrahydropyranyl group and at the C-4' proton of the daunosamine moiety.

TABLE 2

| Proton Compound | 4'-THP* (ppm) | 14-THP* (ppm) | DS4'** (ppm) |
|---|---|---|---|
| 4'-O-PDa | 4.38 | — | 3.62 |
| 4'-O-PDb | 4.72 | — | 3.64 |
| 4'-O-PAa | 4.36 | — | 3.70 |
| 4'-O-PAb | 4.72 | — | 3.70 |

TABLE 1

Physicochemical Properties of Pyranyl Derivatives

| Compounds | 4'-O-PDa | 4'-O-PDb | 4'-14-di-O-PAa | 4', 14-di-O-PAb |
|---|---|---|---|---|
| Analytical data | | | | |
| (1) Elementary analysis () Calcd. %* | C: 60.82 (61.04) H: 6.27 (6.24) N: 2.24 (2.22) | C: 61.48 (61.04) H: 6.37 (6.24) N: 1.97 (2.22) | C: 61.12 (60.89) H: 6.75 (6.50) N: 1.86 (1.92) | C: 61.25 (60.89) H: 6.81 (6.50) N: 1.84 (1.92) |
| (2) Molecular weight | 611.70 | 611.70 | 711.83 | 711.83 |
| (3) Melting point (°C.) | 193~196 (decomp.) | 190~193 (decomp.) | 180~186 (decomp.) | 178~182 (decomp.) |
| (4) Specific rotation C = 0.2 CHCl$_3$ | $[\alpha]_D^{22}$ + 125° | $[\alpha]_D^{22}$ + 162.5° | $[\alpha]_D^{24}$ + 25° | $[\alpha]_D^{24}$ + 125° |
| (5) R$_f$ value** | 0.46 | 0.65 | 0.55 | 0.73 |
| (6) UV visible absorption spectrum (nm) ($E_{1cm}^{1\%}$) | 222s(335),234(515) 252.5(350),289(120) 480(140),496(140) 532(80),576(15) | 222s(330),234.5(485) 252.5(350),290(115) 480(135),498(140) 532(85),576(20) | 220s(320),234.5(480) 253(360),290(110) 480s(145),498(155) 532(110),577(40) | 220s(310),234.5(460) 253(350),290(105) 480s(140),497(150) 532(105),576(40) |

| Compounds | 14-O-PA | 4'-O-PAa | 4'-O-PAb |
|---|---|---|---|
| Analytical data | | | |
| (1) Elementary analysis () Calcd. %* | C: 59.71 (59.52) H: 6.23 (6.10) N: 2.33 (2.17) | C: 59.65 (59.52) H: 6.33 (6.10) N: 2.21 (2.17) | C: 59.71 (59.52) H: 6.24 (6.10) N: 2.05 (2.17) |
| (2) Molecular weight | 627.70   627.70 | 627.70 | 627.70 |
| (3) Melting point (°C.) | 195~202 (decomp.) | 172~177 (decomp.) | 188~192 (decomp.) |
| (4) Specific rotation C = 0.2 CHCl$_3$ | $[\alpha]_D^{24}$ + 162.5° | $[\alpha]_D^{26}$ + 150° | $[\alpha]_D^{25}$ + 150° |
| (5) R$_f$ value** | 0.12 | 0.32 | 0.49 |
| (6) UV visible absorption spectrum (nm) $E_{1cm}^{1\%}$ | 220s(340),234(530) 252.5(400),290(115) 480s(160),497(170) 532(135),577(65) | 220s(350),234(515) 252.5(360),290(120) 480(150),497(160) 532(100),577(30) | 220s(365),234(480) 252(350),290(110) 480s(135),498(140) 531.5(100).580(45) |

*Calculated as monohydrate
**Silica gel TLC: CHCl$_3$:CH$_3$OH = 10:1 (v/v), 26° C. (Merck Co. 60F$_{254}$)

627.70   627.70

With respect to the structure of the compounds 4'-O-PDa, 4'-O-PDb, 4',14-di-O-PAa, 4',14-di-O-PAb, 14-O-PA, 4'-O-PAa and 4'-O-PAb of the present invention, the number of tetrahydropyranyl groups bound to the compounds can be analyzed to be either one or two by the signal intensity of methine proton at C-2 and the methylene proton at the C-3, C-4, C-5 and C-6 positions of the tetrahydropyranyl group. The binding position of the tetrahydropyranyl group can be analyzed by the

| | | | |
|---|---|---|---|
| 4',14-di-O-PAa | 4.38 | 4.70 | 3.60 |
| 4',14-di-O-PAb | 4.72 | 4.72 | 3.66 |
| 14-O-PA | — | 4.71 | 3.48 |
| Daunomycin | — | — | 3.49 |

*THP: Chemical shift at C-2 methine of substituted tetrahydropyranyl group
**DS4': Chemical shift at C-4' methine of daunosamine From the above, the structures of the compounds included within formula I' were determined to be as indicated above.

Characterizing properties for certain other etherified derivatives of general formula I are shown below in Examples 1 to 18.

Biological Properties

The compounds within the scope of formula I have been found to possess both antimicrobial activity and antitumor activity. In addition the 4'-etherified derivatives of formula I wherein $R^1$ is tetrahydropyranyloxy, $C_2$–$C_7$ alkanoyloxy or phenylacetyloxy are useful as intermediates for preparation of the corresponding compounds in which $R^1$ is hydroxyl.

For use as antimicrobial and antitumor agents, the preferred compounds are those of general formula I' and those of general formula I'' in which $R^1$ is hydrogen or hydroxyl.

The compounds of formula I have been found to possess antimicrobial activity against a variety of pathogenic microorganisms. To illustrate such activity, minimum inhibitory concentrations (as determined by the broth dilution method) of representative compounds are shown in Table 3.

TABLE 3

| Test Organisms | Minimum Inhibitory Concentration (MIC, mcg./ml.) | | | |
|---|---|---|---|---|
| | Compound Tested | | | |
| | 4'-O-PDa | 4'-O-PDb | 4'-O-PAa | 4'-O-PAb |
| Staph. aureus FDA 209P | 6.25 | 6.25 | 6.25 | 6.25 |
| Staph. aureus Smith | 12.5 | 3.12 | 6.25 | 6.25 |
| Bacillus subtillis NRRLB-558 | 3.12 | 1.56 | 3.12 | 3.12 |
| Bacillus cereus ATCC 10702 | 6.25 | 6.25 | 6.25 | 6.25 |
| Bacillus megaterium APF | 6.25 | 3.12 | 3.12 | 3.12 |
| Sarcina lutea PCI 1001 | 0.39 | 0.39 | 0.78 | 0.78 |
| Micrococcus flavus FDA 16 | 0.78 | 1.56 | 3.12 | 3.12 |
| Corynebacterium bovis 1810 | 0.78 | 0.78 | 3.12 | 3.12 |
| Pseudomonas aeruginosa A3 | >100 | >50 | >100 | >100 |
| Escherichia coli NIHJ | >100 | >100 | >100 | >100 |
| Mycobacterium smegmatis ATCC 607 | 6.25 | 6.25 | 100 | 100 |
| Candida albicans | >50 | 25 | >100 | >50 |

As indicated by Table 3, the present compounds are useful as antimicrobial agents, particularly against gram-positive bacteria.

A. The tetrahydropyranyl ether derivatives of general formula I' were found to have a marked inhibitory effect on the growth and nucleic acid synthesis of L1210 leukemia cells in culture.

For example, L1210 cells ($5 \times 10^4$ cells/ml.) were inoculated in RPMI 1640 medium (Roswell Park Memorial Institute 1640) containing 20% calf serum and cultivated at 37° C. in the presence of 0.1 and 0.5 µg./ml. of the test compounds in a $CO_2$ incubator. The number of cells were periodically counted and the growth inhibition rate (%) of control was determined as shown in Table 4.

TABLE 4

Growth Inhibitory Effect of Tetrahydropyranyl Derivatives on L1210 Cells in Culture

| Concentration | Inhibition Rate (%) | |
|---|---|---|
| Compounds | 0.1 | 0.5 µg./ml. |
| 4'-O-PDa | 79.2 | 95.0 |
| 4'-O-PDb | 74.6 | 88.8 |
| Daunomycin | 68.8 | 72.7 |
| 4'-O-PAa | 65.9 | 81.1 |
| 4'-O-PAb | 78.1 | 92.9 |
| 14-O-PA | 7.6 | 58.3 |
| 4',14-di-O-PAa | 37.5 | 80.8 |
| 4',14-di-O-PAb | 25.5 | 72.1 |
| Adriamycin | 70.7 | 84.2 |

The effect of the tetrahydropyranyl ether derivatives of formula I' on nucleic acid synthesis was examined as follows:

$1 \times 10^5$ cells/ml. of L1210 cells were suspended in RPMI medium containing 10% calf serum, pre-cultivated at 37° C. for 1 to 2 hours in a $CO_2$ incubator and then the test compounds were added to the medium at various concentrations. After 15 min. of incubation, $^{14}C$-uridine (0.05 µCi/ml.) or $^{14}C$-thymidine (0.05 µCi/ml.) was added and incubated at 37° C. for 60 min. Trichloroacetic acid (TCA) (10%) was added to the incubation medium to stop the reaction and precipitate the acid-insoluble materials, and then the precipitate was washed three times with 5 to 10% TCA dissolved in formic acid. The radioactivity was measured and expressed as 50% inhibition concentration of incorporation.

TABLE 5

50% Inhibition Concentration of $^{14}C$-Thymidine and $^{14}C$-Uridine Incorporation into L1210 Cells in Culture

| | 50% Inhibition Concentration µg./ml. | |
|---|---|---|
| Compounds | Uridine | Thymidine |
| 4'-O-PDa | 0.13 | 0.28 |
| 4'-O-PDb | 0.20 | 0.32 |
| Daunomycin | 0.40 | 0.70 |
| 4'-O-PAa | 0.20 | 0.37 |
| 4'-O-PAb | 0.24 | 0.50 |

TABLE 5-continued

50% Inhibition Concentration of $^{14}$C-Thymidine and $^{14}$C-Uridine Incorporation into L1210 Cells in Culture

| Compounds | 50% Inhibition Concentration μg./ml. | |
|---|---|---|
| | Uridine | Thymidine |
| 14-O-PA | 0.17 | 0.42 |
| 4'-14-di-O-PAa | 0.23 | 0.55 |
| 4',14-di-O-PAb | 0.24 | 0.97 |
| Adriamycin | 0.50 | 2.1 |

B. When tested against various experimental animal tumors, the present compounds show a marked antitumor activity with reduced toxicity relative to adriamycin and daunomycin. Accordingly, the compounds are therapeutically useful in inhibiting the growth of experimental animal tumors.

As an example, BDF$_1$ mice were inoculated intraperitoneally with 1×10$^6$ cells/mouse of L1210 leukemia cells. After 24 hours had elapsed since inoculation, the mice were administered certain of the tetrahydropyranyl ether derivatives of formula I' intraperitoneally once daily for ten consecutive days and observed for a 45 day period. The antitumor activity was shown by the prolongation rate of survival day (T/C, %) to the survival day of control mice injected with physiological saline. The results are shown in Table 6.

TABLE 6

Antitumor Activity of Tetrahydropyranyl Derivatives (T/C, %)

| Compounds | Dose (mg./kg./day) | | | | | |
|---|---|---|---|---|---|---|
| | 5 | 2.5 | 1.25 | 0.6 | 0.3 | 0.15 |
| 4'-O-PDa | >320 | >320 | 122 | 115 | 96 | 90 |
| 4'-O-PDb | >320 | 256 | 122 | 115 | 103 | 90 |
| 4'-O-PAa | — | 173 | 180 | 187 | 120 | 127 |
| 4'-O-PAb | >375 | >360 | >373 | 293 | 160 | 113 |
| 14-O-PA | 142 | 130 | 126 | 113 | 110 | 103 |
| 4',14-di-O-PA | 154 | 115 | 109 | 96 | 103 | 96 |
| 4',14-di-O-PAb | 161 | 109 | 103 | 103 | 96 | 115 |
| Adriamycin | toxic death | 231 | 218 | 230 | 165 | 128 |

From the results of toxic death and body weight loss of the mice in this experiment, it is shown that the tetrahydropyranyl ether derivatives of formula I' are ⅓ to ½ lower in toxicity than the adriamycin and daunomycin starting materials used for their preparation.

C. The marked antitumor effects seen from A and B above were confirmed by the stability of the test compounds on the inactivation by hepatic NADPH-cytochrome P450 reductase. Specifically, NADPH-cytochrome P450 reductase purified from rat liver homogenate was incubated with the tetrahydropyranyl ether derivatives of formula I' at 25° C. for 25 min. in nitrogen gas phase, and the incubation product formed, 7-deoxyaglycone, was determined as shown in Table 7.

TABLE 7

Stability of Tetrahydropyranyl Derivatives on Rat NADPH-Cytochrome P450 Reductase

| Compounds | Product (nmoles/tube) (7-Deoxyaglycone) |
|---|---|
| 4'-O-PDa | 37.3 |
| 4'-O-PDb | 46.6 |
| Daunomycin | 65.8 |
| 4'-O-PAa | 10.9 |
| 4'-O-PAb | 15.8 |
| 14-O-PA | 18.4 |
| 4',14-di-O-PAa | 13.1 |
| 4',14-di-O-PAb | 15.8 |
| Adriamycin | 47.2 |

Composition of reaction mixture:
NADPH        0.2 mM
Tris-HCl (pH 8.0) 0.1 M
Substrate    0.1 mM
Enzyme       4.6 μg./ml
(Tris-HCl = Tris (hydroxymethyl) amino methane)

D. Representative compounds of general formula I" were tested against experimental animal tumors as follows:

CDF$_1$ mice were administered intraperitoneally (i.p.) with 1×10$^5$ cells/mouse of L1210 cells. After 24 hours had elapsed since inoculation, the mice were administered the test compounds intraperitoneally once daily for 10 consecutive days and observed for a 45 day period.

The antitumor activity was shown by the prolongation rate of survival day (T/C, %) to the survival day of control mice injected with physiological saline. The results are shown in Table 8.

TABLE 8

Antitumor Activity (T/C, %) of Etherified Anthracycline Glycoside Derivatives

| Compound** of Example No. | Dose (mg/kg/day) | | | | | |
|---|---|---|---|---|---|---|
| | 5 | 2.5 | 1.25 | 0.625 | 0.31 | 0.15 |
| DAM (for comparison) | Tox. | 138* | 191 | 145 | 132 | 118 |
| ADM (for comparison) | 189* | 351 | 272 | 239 | 147 | 130 |
| 1-a | 225 | 239 | 228 | 195 | 203 | — |
| 1-b | 241 | 218 | 220 | 184 | 145 | — |
| 4 | 314 | 360 | 179 | 136 | 111 | 105 |
| 5-a | 212 | 288 | 189 | 135 | 115 | 115 |
| 5-b | 256 | 230 | 154 | 141 | 128 | 122 |
| 6 | 141 | 118 | 118 | 106 | 88 | 100 |
| 7-a | 108 | 277 | 145 | 127 | 101 | 96 |
| 7-b | 211 | 151 | 157 | 127 | 108 | 108 |
| 8-a | 163 | 138 | 125 | 119 | 100 | 100 |
| 8-b | 288 | 138 | 119 | 106 | 100 | 100 |
| 9-a | 257 | 151 | 125 | 112 | 105 | 105 |
| 9-b | 303 | 158 | 118 | 105 | 118 | 99 |
| 10-a | 125 | 125 | 118 | 99 | 92 | 105 |
| 10-b | 118 | 105 | 112 | 112 | 105 | 105 |
| 11-a | 184 | 125 | 118 | 105 | 99 | 105 |
| 11-b | 145 | 125 | 105 | 105 | 105 | 105 |
| 12 | 346 | 160 | 111 | 111 | 105 | 99 |
| 14-a | 232 | 125 | 106 | 100 | 100 | 100 |
| 14-b | 463 | 131 | 113 | 106 | 100 | 94 |
| 15 | 131 | 106 | 100 | 100 | 100 | 100 |
| 16-a | 217 | 157 | 102 | 104 | 96 | 96 |
| 16-b | 247 | 133 | 112 | 108 | 96 | 90 |
| 18-a | 144 | 116 | 116 | 110 | 103 | 110 |
| 18-b | 188 | 151 | 110 | 110 | 96 | 103 |
| 17-a | 156 | 119 | 100 | 100 | 100 | 100 |
| 17-b | 188 | 113 | 106 | 100 | 100 | 100 |

Note:
DAM = daunomycin, ADM = adriamycin
*: toxic
**use of the letter "a" or "b" after a number refers to isomer a or isomer b prepared in that example.

E. The inhibitory effect of representative compounds of general formula I" on the growth and nucleic acid biosynthesis in cultured L1210 leukemia cells was examined as follows:

L1210 cells ($5 \times 10^4$ cells/ml.) were inoculated in RPMI 1640 medium (Roswell Park Memorial Institute 1640) containing 20% calf serum and cultivated at 37° C. in the presence of 0.1 and 0.5 μg/ml. of the test compounds in a $CO_2$ incubator. The number of cells were periodically counted and the 50% growth inhibition concentration of control was determined as shown in Table 9.

Furthermore, the 50% inhibition concentration of the test compounds on nucleic acid biosynthesis was examined as follows:

$1 \times 10^5$ cells/ml. of L1210 cells were suspended in RPMI medium containing 10% calf serum, pre-cultivated at 37° C. for 1 to 2 hours in a $CO_2$ incubator and then the test compounds were added to the medium at various concentrations. After 15 min. incubation, $^{14}C$-uridine (0.05 μCi/ml.) or $^{14}C$-thymidine (0.05 μCi/ml.) was added and incubated at 37° C. for 60 min. 10% trichloroacetic acid (TCA) was added to the incubation medium to stop reaction and precipitate the acid-insoluble materials, and then the precipitate was washed three times with 5 to 10% TCA, soluble in formic acid. The radioactivity in the acid-insoluble materials was measured and expressed as 50% inhibition concentration of incorporation. The results are also shown in Table 9.

TABLE 9

Inhibitory effect on the growth and nucleic acid biosynthesis in cultured L1210 cells.

| Compound* of Example No. | $ID_{50}$ (g/ml) against L1210 cells | | |
|---|---|---|---|
| | growth (after 2 days) | DNA | RNA |
| DAM | 0.036 | 0.3 | 1.7 |
| ADM | 0.018 | 1.25 | 0.49 |
| 5-a | 0.015 | 0.5 | 0.19 |
| 5-b | 0.015 | 0.54 | 0.19 |
| 6 | 0.04 | 0.56 | 0.29 |
| 7-a | 0.015 | 0.36 | 0.13 |
| 7-b | 0.01 | 0.43 | 0.18 |
| 8-a | 0.04 | 1.9 | 0.52 |
| 8-b | 0.05 | 1.5 | 0.37 |
| 9-a | 0.025 | 0.85 | 0.32 |
| 9-b | 0.03 | 0.5 | 0.15 |
| 10-a | 0.38 | >10.0 | 2.5 |
| 10-b | 0.52 | >10.0 | 2.8 |
| 11-a | 0.04 | 1.3 | 0.43 |
| 11-b | 0.06 | 1.3 | 0.32 |
| 12 | 0.017 | 0.41 | 0.17 |
| 14-a | 0.04 | 0.62 | 0.3 |
| 14-b | 0.25 | 0.8 | 0.33 |
| 15 | 0.095 | 0.93 | 0.44 |
| 16-a | 0.025 | 0.34 | 0.13 |
| 16-b | 0.03 | 0.65 | 0.29 |
| 18-a | 0.08 | 0.93 | 0.37 |
| 18-b | 0.075 | 1.4 | 0.6 |
| 17-a | 0.08 | 1.4 | 0.5 |
| 17-b | 0.06 | 0.8 | 0.28 |

Note:
DAM = daunomycin, ADM = adriamycin
*: use of the letter "a" or "b" after a number refers to isomer a or b prepared in that example The data from Tables 8 and 9 indicate that the derivatives of general formula I″ are ½ to ⅓ lower in toxicity than the parent adriamycin and daunomycin compounds.

Therapeutic Use

As mentioned above, the compounds of formula I and their nontoxic acid addition salts are novel antibiotics, useful in both human and veterinary medicine, and also possess marked inhibitory action against malignant tumors in experimental animals, including both solid and ascitic types.

According to one aspect of the invention, a method is provied for therapeutically treating a mammalian host affected by a microbial infection (particularly a gram-positive bacterial infection) or an experimental animal host affected by a malignant tumor (i.e. a solid- or ascitic-type tumor such as L1210 leukemia) which comprises administering to said host an effective antimicrobial or tumor-inhibiting dose of a compound of formula I, or a nontoxic acid addition salt thereof.

According to another aspect of the invention, a pharmaceutical composition is provided which comprises a thereapeutically effective antimicrobial or tumor-inhibiting amount of a compound of formula I, or a nontoxic acid addition salt thereof, in combination with a pharmaceutical carrier or diluent. Such compositions may be made up in any pharmaceutical form appropriate for parenteral administration.

Preparations for parenteral administration include sterile aqueous or non-aqueous solutions, suspensions or emulsions. They may also be manufactured in the form of sterile solid compositions which can be dissolved in sterile water, physiological saline or some other sterile injectable medium immediately before use.

It will be appreciated that the actual preferred dosage amounts used will vary according to the particular compound being used, the particular composition formulated, the mode of application and the particular situs, host and disease being treated. In general the compounds are injected intraperitoneally, intravenously, subcutaneously or locally. Many factors that modify the action of the drug will be taken into account by those skilled in the art, for example, age, body weight, sex, diet, time of administration, route of administration, rate of excretion, condition of the host, drug combinations, reaction sensitivites and severity of the disease. Administration can be carried out continuously or periodically within the maximum tolerated dose. Optimal application rates for a given set of conditions can be ascertained by those skilled in the art using conventional dosage determination tests in view of the above guidelines.

For use as an antimicrobial agent, the compounds are in general administered so that the concentration of active ingredient is greater than the minimum inhibitory concentration for the particular organism being treated.

The following examples are provided for illustrative purposes only and are not intended to limit the scope of the invention. In the examples, the ratio of solvent in a mixture is indicated in the ratio of volume to volume, the % of liquid to liquid is indicated as v/v and the % of solid to liquid is indicated as w/v unless otherwise mentioned.

Preparation of Starting Materials

Prior to the description of the Examples, as an example for preparing 14-0-acylated adriamycin which is to be used as a starting material for the preparation of 14-0-acyl-4'-0-etherified adriamycin, the experimental embodiment of the preparation of 14-0-acetyl adriamycin will be mentioned as follows. Other 14-0-acylated adriamycins to be used as starting materials in the present invention can be prepared according to this experiment.

Preparation 1

(1) 14 Bromodaunomycin-dimethylketal hydrochloride 230 mg (0.41 mmoles) of daunomycin hydrochloride was dissolved in 10 ml of absolute methanol, adding 20 ml of dioxane. The mixture was allowed to stand for 2 to 3 hours at 22° to 23° C., followed by dropwise addition of 0.88 ml (0.55 mmoles) of 10% chloroform containing bromine aqueous solution while stirring. The reaction mixture was concentrated to about 5 ml under reduced pressure and thereafter 15 ml of dry ether was added to obtain an orange-red precipitate by filtration. The precipitate was washed three times with 3 ml of ether and dried. 277 Mg of hydrochloride salt of 14-0-bromodaunomycin-dimethyl ketal having a melting point of 175° to 178° C. was obtained with a yield of 98%.

(2) p-Toluenesulfonate or hydrochloride salt of 14-0-acetyl adriamycin 207 mg (0.3 mmoles) of 14-bromodaunomycin dimethylketal hydrochloride salt was suspended in 100 ml of dry acetone. Thereafter 0.4 g of dry sodium acetate was added and the mixture was refluxed for 1 hour with agitation. The reaction mixture was filtered to remove impurities, and the filtrate was concentrated under reduced pressure. The residue was distributed in a mixture containing 30 ml of chloroform and 20 ml of 0.05 N hydrochloric acid. The acidic aqueous layer thus obtained was neutralized with sodium hydrogen carbonate and then re-extracted with chloroform. The reddish chloroform layer was dried over anhydrous sodium sulfate and concentrated to about 5 ml under reduced pressure, and an orange precipitate of salt form was formed by adding 40 mg of p-toluenesulfonic acid or an equivalent amount of hydrochloric acid, according to the salification method of the corresponding acid addition salt. The resulting precipitate was filtered and washed with ether, and 160 mg of p-toluenesulfonate salt of 14-0-acetyl adriamycin having a melting point at 165° to 168° C. was obtained. In the case of hydrochloride salt, about the same amount of compound can be obtained.

For the convenience of reading and locating the attributes of NMR, the configuration of adriamycin with indications showing the position of the carbon atoms is indicated below.

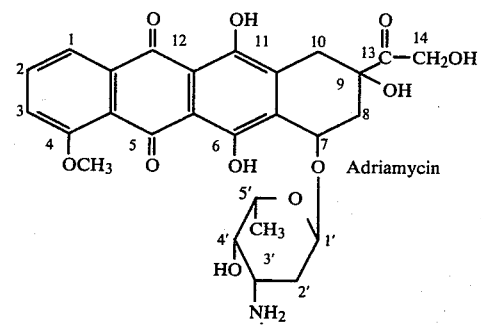

The $R^1$ and $R^2$ substituents for the derivatives of Examples 1–18 are shown in the following table.

TABLE 10

| Compounds | No. | $R^1$ | $R^2$ |
|---|---|---|---|
| 14-O-acetyl-4'-O-tetrahydropyranyl-ADM (a) | 1-a | —O—C(=O)—CH₃ | (tetrahydropyranyl) |
| 14-O-acetyl-4'-O-tetrahydropyranyl-ADM (b) | 1-b | " | " |
| 4'-O-(tetrahydrofuranyl)-ADM | 4 | —OH | (tetrahydrofuranyl) |
| 4'-O-(tetrahydrofuranyl)-ADM (a) | 5-a | " | " |
| 4'-O-(tetrahydrofuranyl)-ADM (b) | 5-b | " | " |
| 4'-O-(6-acetoxymethyltetrahydropyranyl)-ADM | 6 | " | (tetrahydropyranyl)—CH₂—O—C(=O)—CH₃ |
| 4'-O-(1-ethoxyethyl)-ADM (a) | 7-a | " | —CH(CH₃)—O—CH₂CH₃ |
| 4'-O-(1-ethoxyethyl)-ADM (b) | 7-b | —OH | —CH(CH₃)—O—CH₂CH₃ |
| 4'-O-(1-butyloxyethyl)-ADM (a) | 8-a | " | —CH(CH₃)—O—CH₂(CH₂)₂CH₃ |
| 4'-O-(1-butyloxyethyl)-ADM (b) | 8-b | " | " |
| 4'-O-(1-isobutyloxyethyl)-ADM (a) | 9-a | " | —CH(CH₃)—O—CH₂CH(CH₃)₂ |
| 4'-O-(1-isobutyloxyethyl)-ADM (b) | 9-b | " | " |

TABLE 10-continued

| Compounds | No. | R¹ | R² |
|---|---|---|---|
| 4'-O-(1-(6-methyl-heptyloxy)ethyl)-ADM (a) | 10-a | " | $-\underset{\underset{CH_3}{|}}{CH}-O-CH_2(CH_2)_4CH\underset{CH_3}{\overset{CH_3}{<}}$ |
| 4'-O-(1-(6-methyl-heptyloxy)ethyl)-ADM (b) | 10-b | " | " |
| 4'-O-(1-cyclo-hexyloxyethyl)-ADM (a) | 11-a | " | $-\underset{\underset{CH_3}{|}}{CH}-O-\langle H \rangle$ |
| 4'-O-(1-cyclo-hexyloxyethyl)-ADM (b) | 11-b | " | " |
| 4'-O-(tetra-hydrofuranyl)-DAM | 12 | —H | (tetrahydrofuranyl) |
| 4'-O-(6-methoxy-tetrahydro-pyranyl)-DAM | 14-a | " | (6-methoxy-tetrahydropyranyl)-OCH₃ |
| 4'-O-(6-methoxy-tetrahydro-pyranyl)-DAM (b) | 14-b | " | " |
| 4'-O-(6-acetoxy-methyltetra-hydropyranyl)-DAM | 13 | H | (tetrahydropyranyl)-CH₂—O—$\overset{\overset{O}{\|}}{C}$—CH₃ |
| 4'-O-(6-carbo-methoxytetra-hydropyranyl)-DAM | 15 | " | (tetrahydropyranyl)-$\overset{\overset{O}{\|}}{C}$—OCH₃ |
| 4'-O-(1-ethoxy-ethyl)-DAM (a) | 16-a | " | $-\underset{\underset{CH_3}{|}}{CH}-O-CH_2CH_3$ |
| 4'-O-(1-ethoxy-ethyl)-DAM (b) | 16-b | " | " |
| 4'-O-(1-butyloxy-ethyl)-DAM (a) | 18-a | " | $-\underset{\underset{CH_3}{|}}{CH}-O-CH_2(CH_2)_2CH_3$ |
| 4'-O-(1-butyloxy-ethyl)-DAM (b) | 18-b | H | $-\underset{\underset{CH_3}{|}}{CH}-O-CH_2(CH_2)_2CH_3$ |
| 4'-O-(1-iso-butyloxyethyl)-DAM (a) | 17-a | " | $-\underset{\underset{CH_3}{|}}{CH}-O-CH_2CH\underset{CH_3}{\overset{CH_3}{<}}$ |
| 4'-O-(1-iso-butyloxyethyl)-DAM (b) | 17-b | " | " |

EXAMPLE 1

Process for producing 14-O-acetyl-4'-O-tetrahydropyranyl adriamycin a and b 155 mg (or equivalent amount of hydrochloride salt) of p-toluenesulfonate salt of 14-O-acetyl adriamycin was dissolved in 2.0 ml of dried dimethylformamide. There was then added 2.0 ml of 3,4-dihydro-2H-pyran and a small amount of p-toluenesulfonic acid, and the mixture was allowed to stand at room temperature overnight. By observing the product and the residual initial material on a silica gel thin-layer chromatography (solvent system; chloroform-methanol=7:1), the formation of two new compounds having Rf values at 0.24 and 0.36 can be detected by the disappearance of the initial material having a Rf value of 0.04. The reaction mixture was extracted with 20 ml of chloroform and water. To the aqueous layer was added an amount of sodium hydrogen carbonate to adjust the pH of the aqueous layer at 7 to 8, and it was extracted with chloroform. After the chloroform extract was dried and concentrated under reduced pressure, the resulting residue was applied to a preparative silica gel thin-layer plate and developed by a chloroform-methanol mixture (7:1) to obtain 14-O-acetyl-4'-O-tetrahydropyranyl adriamycin a and b respectively as follows:

Compound a (Rf: 0.24) yield 24 mg

Molecular weight: 669.68.
Melting point (°C.): 185–195.

| Specific rotation (C = 0.2 in chloroform) | |
|---|---|
| $[\alpha]_D^{22°}$ C. | +183° |
| UV and visible absorption spectra in methanol | 222s(335), 234(515) 253(360), 289(130) 480(145), 496(145) |

-continued

| | |
|---|---|
| λmax$_{nm}$(E$_{1cm}^{1\%}$) | 532(90), 576(20) |

PMR (CDCl$_3$, ppm): 1.28(6'—H), 1.50–1.85 (pyran at 3-H to 5-H), 2.21(OAc), 4.05(4'-OMe), 4.42(pyran, anomeric), 5.18(14-H), 5.26(1'-H), 5.54(7-H), 7.27–8.03 (1-H-3-H).

Compound b (Rf: 0.36) yield 34 mg

Molecular weight: 669.68.
Melting point (°C.): 180–190.

| | |
|---|---|
| Specific rotation (C = 0.2 in chloroform) | |
| [α]$_D^{22°}$ C. | +154° |
| UV and visible absorption spectra in methanol | 222s(335), 234(510) |
| | 253(350), 289(130) |
| | 481(140), 495(140) |
| λmax$_{nm}$(E$_{1cm}^{1\%}$) | 532(85), 576(20) |

PMR (CDCl$_3$, ppm): 1.37(6'-H), 1.40–2.00 (pyran), 2.21(OAc), 4.08(4-OMe), 4.75(pyran, anomeric), 5.18(14-H), 5.25(1'-H), 5.53(7-H), 7.30–8.06(1-H-3H).

EXAMPLE 2

Process for producing 14-O-isobutyloyl-4'-O-tetrahydropyranyl adriamycin a and b 104 mg (0.13 mmoles) of p-toluenesulfonate of 14-O-isobutyloyl adriamycin was dissolved in 2.0 ml of dried dimethylformamide, adding 2.0 ml of dihydropyran and p-toluenesulfonic acid as a catalyst, and allowed to stand for 15 hours at room temperature. The products were detected on a thin-layer chromatogram (solvent system, chloroform-methanol=9:1) at Rf values of 0.38 and 0.45. The reaction mixture was poured into 20 ml of water, neutralized with sodium hydrogen carbonate and extracted with 30 ml of chloroform. The chloroform layer was dried over anhydrous sodium sulfate, and concentrated to dryness under reduced pressure. The resulting residue was developed and purified by thin-layer chromatography. 22.5 mg of red powder of compound a was obtained from the fraction of Rf 0.38.

Yield 24%, Melting point (°C.): 155–161.
PMR (CDCl$_3$, ppm): 1.24(H-6'), 1.29(isobutyl), 4.06(4'-OMe), 4.40(pyran, anomeric), 5.10(H-14), 5.25(1'-H), 5.51(7-H), 7.30–8.07(1-H-3-H).

And, 22.7 mg of red powder of compound b was obtained from the fraction of Rf 0.45.

Yield 24%, Melting point (°C.): 169°–174.
PMR (CDCl$_3$, ppm): 1.25(isobutyl), 1.37(6'-H), 1.40–2.00(THP), 4.08 (4-OMe), 4.75(pyran, anomeric), 5.22 (14-H), 5.25(1'-H), 5.55(7-H), 7.29–8.10(1-H-3-H).

EXAMPLE 3

Process for producing 14-O-phenylacetyl-4'-O-tetrahydropyranyl adriamycin a and b 80 mg 0.096 mmoles) of p-toluenesulfonate of 14-O-phenylacetyl adriamycin was dissolved in 2.5 ml of dried dimethylformamide, adding 0.5 ml of dihydropyran and a small amount of p-toluenesulfonic acid and allowed to stand at room temperature. The formation of the products having Rf values of 0.39 and 0.48 was confirmed by thin-layer chromatography using solvent system of chloroform-methanol (9:1), and the initial material apparently disappeared after 4 hours. The reaction mixture was poured into 20 ml of 1% sodium hydrogen carbonate aqueous solution and extracted with 30 ml and again 10 ml of chloroform. The chloroform layers were combined, washed four times with water, dried over anhydrous sodium sulfate, and concentrated to dryness. The resulting solid was developed by preparative thin-layer chromatography using a silica gel plate (2 mm thickness, 20×20 cm) and a solvent system of chloroform-methanol (9:1) to purify. The band of Rf 0.39 was scratched out from the thin-layer, extracted with a chloroform-methanol mixture (1:1), and concentrated to dryness. 27.0 mg of compound a was obtained as red powder.

Yield 37%, Melting point (°C.): 156–163.
PMR (CDCl$_3$, ppm): 1.25(H-6'), 1.40–2.00(tetrahydropyran), 3.80 and 7.36

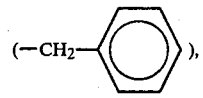

4.02(4-OMe), 4.35(pyran, anomeric), 5.21 (H-14), 5.25(1'-H), 5.50(7-H), 7.30–8.02(1H-3-H).

20.2 mg of compound b was obtained as red powder from the fraction of Rf 0.48 according to the method for compound a.

Yield 28%, Melting point (°C.): 159–165.
PMR (CDCl$_3$, ppm): 1.37(6'-H), 1.45–2.00(pyran), 3.80 and 7.32

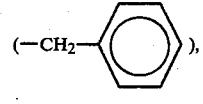

4.05(4-OMe), 4.73(pyran, anomeric), 5.25(14H, 1'-H), 5.50(7-H), 7.30–8.06(1-H-3-H).

EXAMPLE 4

Process for producing 4'-O-tetrahydrofuranyl adriamycin (a) 190 mg (0.25 mmoles) of 14-O-acetyl adriamycin p-toluenesulfonate was dissolved in 10 ml of dried dimethylformamide, adding 0.4 ml of dihydrofuran and p-toluenesulfonic acid as a catalyst, and allowed to stand for 3.5 hours at room temperature (4'-O-tetrahydrofuranylation). The formation of the reaction product having an Rf of 0.24 to 0.27 and the disappearance of the initial material were observed by silica gel thin-layer chromatography using a solvent system of chloroform-methanol (9:1). The reaction mixture was poured into 100 ml of water, neutralized with sodium hydrogen carbonate and extracted with 60 ml of chloroform. The chloroform layer was dried over anhydrous sodium sulfate, concentrated to dryness under reduced pressure and developed by preparative thin-layer chromatography using two silica gel plates (20×20 cm, 2 mm thickness) and a solvent system of chloroform-methanol (9:1). The band of Rf 0.24 to 0.27 was scratched out from the silica gel thin-layer, extracted with a chloroform-methanol mixture (1:1), and concentrated to dryness. 66.8 mg of 14-O-acetyl-4'-O-tetrahydrofuranyl adriamycin was obtained as a red solid.

Yield 40%.

PMR (CDCl$_3$, ppm): 1.23–1.34(6'-H), 1.70–2.12(furan), 2.20, 2.22(acetyl), 4.06(4-OMe), 5.20(14-H), 5.36(furan, anomeric), 5.51(7-H), 7.27–8.06(1-H–3-H).

(b) 41.0 mg of 14-O-acetyl-4'-O-tetrahydrofuranyl adriamycin was dissolved in 10 ml of methanol and 3 ml of water while stirring, adding 10% potassium carbonate solution to change the solution to blue-violet color (pH 10–11) and allowed to stand for 30 min. (hydrolysis). Descending of the Rf value was observed by silica gel thin-layer chromatography using a solvent system of chloroform-methanol (1:1). The reaction mixture was neutralized by adding a small piece of dry-ice and extracted with chloroform. The chloroform layer was washed with water, dried and concentrated to dryness. The resulting residue was purified by preparative thin-layer chromatography according to the method of (a). 16.3 mg of 4'-O-tetrahydrofuranyl adriamycin was obtained as red powder.

Yield 43%, Melting point (°C.): 189–194 (decomposition).

PMR (CDCl$_3$, ppm): 1.25–1.27(6'-H), 1.67–2.30(furan), 4.07–4.08(4H), 5.17 and 5.38(furan, anomeric), 5.30(1'-H), 5.51(7-H), 7.30–8.07(1-H–3-H).

EXAMPLE 5

Process for producing 4'-O-tetrahydrofuranyl adriamycin a and b 40 mg of 4'-O-tetrahydrofuranyl adriamycin obtained in Example 4 was preparatively re-chromatographed using silica gel (Merck Co.) and a solvent system of chloroform-methanol (15:1). An amount less than 1 mg per plate was applied on a silica gel plate (0.25 mm thickness, 20×20 cm), and developed three times to achieve good separation. The band corresponding to Rf 0.20 was scratched out from the silica gel plate, eluted with chloroform-methanol (1:1) and concentrated to dryness. The resulting compound a weighed 11.0 mg and contains the following properties.

Melting point (°C.): 189–191, $[\alpha]_D$+175° (CHCl$_3$, C=0.2).

PMR (CDCl$_3$, ppm): 1.25(6'-H), 1.67–2.37(furan), 4.07(4-H), 5.17(furan, anomeric), 5.30(1'-H), 5.51(7-H), 7.30–8.06(1-H–3-H).

The fractions of Rf 0.22 weighed 12.1 mg of compound b, and its properties are as follows:

Melting point (°C.): 190–192, $[\alpha]_D$+150° (CHCl$_3$, C=0.2).

PMR (CDCl$_3$, ppm): 1.27(6'-H), 1.67–2.30(furan), 4.08(4-H), 5.30(1'-H), 5.38(furan, anomeric), 5.51(7-H), 7.30–8.07(1-H–3-H).

EXAMPLE 6

Process for producing 4'-O-(6-acetoxymethyltetrahydropyranyl) adriamycin (a) 150 mg (0.18 mmoles) of p-toluenesulfonate of 14-O-phenylacetyl adriamycin was dissolved in 2.0 ml of dry dimethylformamide, adding 0.2 ml of 2-acetoxymethyl-3,4-dihydro-2H-pyran and 15 mg (0.09 mmoles) of p-toluenesulfonic acid and allowed to stand for 24 hours at room temperature [4'-O-(6-acetoxymethyltetrahydropyranylation)]. The spots of the initial material and the product having a Rf 0.51 was detected in the reaction mixture by silica gel thin-layer chromatography using a solvent system of chloroform-methanol (9:1). The reaction mixture was poured into 20 ml of water, neutralized with sodium hydrogen carbonate and extracted twice with 30 ml of chloroform. The chloroform layer was dried over anhydrous sodium sulfate and chromatographed on 10 g of silica gel column (Merck Co. Kiesel gel #100), and the column was washed with 100 ml of chloroform. The product was successively eluted with a chloroform-methanol mixture (10:1) and detected by thin-layer chromatography. The fraction of Rf 0.51 was collected, concentrated to dryness, and 100.2 mg of 14-O-phenylacetyl-4'-O-(6-acetoxymethyltetrahydropyranyl) adriamycin was obtained as red solid.

Yield 68%.

PMR (CDCl$_3$, ppm): 1.24–1.34(6'-H), 2.08(acetyl), 3.83, 7.40(phenylacetyl), 4.08 (4'-H), 4.95(pyran, anomeric), 5.25(14-H), 5.54(7-H), 7.30–8.08(1-H–3-H).

(b) Then, the substance obtained above was dissolved in 20 ml of acetone with agitation, adding 10 ml of water and 0.5 ml of 10% potassium carbonate, and hydrolyzed for 30 min. The product of Rf 0.41 was observed on a thin-layer chromatogram. A piece of dryice was added to the reaction mixture for neutralizing and distilled to remove the acetone under reduced pressure. The resulting aqueous layer was extracted three times with 10 ml of chloroform respectively. The chloroform layers were combined, washed with water, dried over anhydrous sodium sulfate, and concentrated to dryness to obtain a red solid. The solid was further purified by preparative thin-layer chromatography using silica gel (Merck Co. 2 mm thickness and 20×20 cm, one plate) and a solvent system of chloroform-methanol (9:1), and re-extracted from the fraction of Rf 0.41. 26.9 mg of 4'-O-(6-acetoxymethyltetrahydropyranyl) adriamycin was obtained as red powder.

Yield 31%, Melting point (°C.): 174–178.

PMR (CDCl$_3$, ppm): 1.19–1.40(6'-H), 2.06, 2.10 (OAc), 4.11(4-OMe), 4.78(14-H), 5.55(7-H), 7.35–8.10(1-H–3-H).

EXAMPLE 7

Process for producing 4'-O-(1-ethyloxyethyl) adriamycin a and b (a) 200 mg of p-toluenesulfonate of 14-O-phenylacetyl adriamycin was dissolved in 4.0 ml of dry dimethyl formamide, adding 0.2 ml of ethyl vinyl ether and p-toluenesulfonic acid as a catalyst, and allowed to stand for 1.5 hours at room temperature (4'-O-ethyloxyethylation). By silica gel thin-layer chromatography (solvent system; chloroform-methanol=9:1) of the reaction mixture, it was confirmed that the initial material disappeared and new products of Rf 0.36 and 0.39 were formed. The reaction mixture was poured into 20 ml of water, adding sodium hydrogen carbonate to adjust the pH at 8, and extracted with 60 ml of chloroform. The chloroform layer was dried over anhydrous sodium sulfate and concentrated under reduced pressure to obtain a red material. After purifying the material by preparative thin-layer chromatography using silica gel (2 mm thickness, 20×20 cm, 2 plates) and a solvent system of chloroform-methanol (9:1), 134 mg of 14-O-phenylacetyl-4'-O-(1-ethyloxyethyl) adriamycin was obtained from the band of Rf 0.36–0.39 as red powder.

Yield 76%.

PMR (CDCl$_3$, ppm): 1.21, 3.62(1'-O-ethyl), 1.40 (2'-H), 3.81, 7.38(phenylacetyl), 4.02(4-O-methyl), 5.64, 5.94(1'-H), 5.24(14-H), 5.50(7-H), 7.25–8.02(1H-3H).

(b) Then, the compound obtained above was dissolved in 40 ml of acetone, adding 20 ml of water and 150 mg of anhydrous potassium carbonate and agitated well (hydrolysis). It was confirmed by silica gel thin-layer chromatography (solvent system, chloroform-methanol=9:1) that the substances of Rf 0.36 and 0.39 gradually disappeared and new products of Rf 0.28 and 0.21 were formed. After 20 min. of reaction, the reaction mixture was neutralized with a piece of dry-ice and distilled to remove the acetone. The resulting aqueous layer was extracted twice with 30 ml of chloroform respectively, and the chloroform layer was washed with water, dried over anhydrous sodium sulfate and concentrated to obtain a red residue. According to the same method as mentioned above, the residue was purified by preparative silica gel thin-layer chromatography using a chloroform-methanol mixture (once with 15:1 and twice 9:1 to achieve good separation). The band of Rf 0.21 was scratched out from silica gel thin-layer and extracted with a chloroform-methanol mixture (1:1), and the extract was concentrated to obtain 13.0 mg of red powder of 4'-O-(1-ethyloxyethyl) adriamycin a.

Yield 13%, Melting point (°C.): 205–215.

PMR (CDCl$_3$, ppm): 1.15, 3.58(1-OEt), 1.40(2'-H), 3.58(2'-H), 4.06(4-OMe), 4.65(1'-H), 4.76(14-H), 5.25 (1'-H), 5.51(7-H), 7.25–8.07 (1-H–3-H).

11.2 mg of 4'-O-(1-ethyloxyethyl) adriamycin b was obtained from the band of Rf 0.28.

Yield 11%, Melting point (°C.): 190–200.

PMR (CDCl$_3$, ppm): 1.22, 3.63(1'-OEt), 4.08(4-H), 4.76(14-H), 4.93(1'-H), 5.27 (1'-H), 5.50(7-H), 7.22–8.88 (1-H–3-H).

EXAMPLE 8

Process for producing 4'-O-(1-butyloxyethyl) adriamycin a and b (a) 145.6 mg of p-toluenesulfonate of 14-acetyl adriamycin was dissolved in a mixture of 2 ml of absolute DMSO and 4 ml of absolute dioxane, adding 1.6 ml of n-butyl vinyl ether and further adding 0.396 ml of 0.1 N p-toluenesulfonic acid-dioxane solution under ice-cold conditions. After agitation for 35 min. at room temperature, the reaction mixture was poured into 50 ml of ethylacetate and washed twice with 30 ml of 1% sodium hydrogen carbonate solution respectively and three times with 30 ml of 5% sodium chloride aqueous solution respectively. The aqueous layer was extracted with 50 ml of ethylacetate, and the solvent extracts were combined and dried over anhydrous sodium sulfate, and concentrated under reduced pressure to obtain an oily substance.

The oily substance was chromatographed on the silica gel column (Merck Art. 7734, 4 g, solvent: (1) CHCl$_3$ 60 ml, (2) CHCl$_3$:methanol=10:1 30 ml) to obtain 141 mg from the eluate of the chloroformmethanol mixture. This product was further purified by preparative thin-layer chromatography (Merck Art. 5744, solvent system: CHCl$_3$:methanol=10:1) to obtain 14-O-acetyl-4'-O-(1-butyloxyethyl) adriamycin a and b.

Compound a: 40.5 mg.

Compound b: 33.5 mg.

(b) Deacetylation 40.5 mg of 14-O-acetyl-4'-O-(1-butyloxyethyl)adriamycin b was dissolved in 4 ml of methanol and 1 ml of water, and adding 0.23 ml of 1 N potassium carbonate aqueous solution to change the solution to blue-violet color. After 8 min. of reaction, the reaction mixture was neutralized with a piece of dry-ice, adding 60 ml of water, extracted with 30 ml and 20 ml×3 of chloroform, dried over anhydrous sodium sulfate and concentrated under reduced pressure. By preparative thin-layer chromatography (Merck Art. 5744, solvent system: CHCl$_3$:methanol=10:1), 14.2 mg of 4'-O-(1-butyloxyethyl) adriamycin b and 10.7 mg of compound a were obtained.

| Compound a | | |
|---|---|---|
| Melting point (°C.): | 168–175 | |
| Specific rotation (C = 0.1 in chloroform) [α]$_D^{25}$: | +157° | |
| UV and visible absorption spectra in methanol λmax$_{nm}$(E$_{1cm}^{1\%}$): | 234(585), 251(405) 288(155), 480(187) 495(190), 530(116) 575(19) | |
| PMR (CDCl$_3$, ppm): | 0.92 (t, 3H) | —CH$_2$CH$_3$ |
| | 1.31 (d, 3H) | C5'-CH$_3$ |
| | 1.38 (d, 3H) | C4'-OCHCH$_3$ |
| | 2.91 (d, 1H) | ⎫ |
| | 3.21 (d, 1H) | ⎬ C10-CH$_2$ |
| | 4.03 (s, 3H) | C4-OCH$_3$ |
| | 4.74 (s, 2H) | C14-CH$_2$ |
| | 4.89 (q, 1H) | C4'-OCHCH$_3$ |
| | 5.22 (bs, 1H) | C7-H |
| | 5.48 (bs, 1H) | C1'-H |
| | 7.25–7.98 (m, 3H) | aromatic proton |

| Compound b | | |
|---|---|---|
| Melting point (°C.): | 155–160 | |
| Specific rotation (C = 0.1 in chloroform) [α]$_D^{25}$: | +188° | |
| UV and visible absorption spectra in methanol λmax$_{nm}$(E$_{1cm}^{1\%}$): | 234(533), 251(371) 288(140), 480(168) 495(172), 530(106) 575(19) | |
| PMR (CDCl$_3$, ppm): | 0.91 (t, 3H) | —CH$_2$CH$_3$ |
| | 1.27 (d, 3H) | C5'-CH$_3$ |
| | 1.40 (d, 3H) | C4'-OCHCH$_3$ |
| | 2.95 (d, 1H) | ⎫ |
| | 3.26 (d, 1H) | ⎬ C10-CH$_2$ |
| | 4.06 (s, 3H) | C4-OCH$_3$ |
| | 4.61 (q, 1H) | C4'-OCHCH$_3$ |
| | 4.74 (s, 2H) | C14-CH$_2$ |
| | 5.27 (bs, 1H) | C7-H |
| | 5.50 (bs, 1H) | C1'-H |
| | 7.31–8.02 (m, 3H) | aromatic proton |

EXAMPLE 9

Process for producing 4'-O-(1-isobutyloxy) adriamycin a and b (a) 150 mg of p-toluenesulfonate of 14-O-acetyl adriamycin was dissolved in 3 ml of anhydrous dioxane and 1.5 ml of anhydrous dimethylsulfoxide, adding 0.7 ml of isobutyl vinyl ether and 0.3 ml of 0.1 N p-toluenesulfonic acid-dioxane solution, and agitated for 40 min. at room temperature (23° C.). The reaction mixture was diluted with 50 ml of ethylacetate, washed subsequently with 1% sodium hydrogen carbonate aqueous solution (30 ml×2) and water (30 ml×2), dried over anhydrous sodium sulfate and concentrated under reduced pressure. The resulting oily substance was chromatographed on silica gel column (Merck Art. 7734, 4 g; CHCl$_3$→CHCl$_3$:methanol=10:1), and the fractions containing the main product were collected and concentrated to dryness to obtain 125.5 mg of orange powder. The powder was subjected to preparative thin-layer chromatography (Merck Art. 5744, 12 plates, CHCl$_3$:methanol=10:1) to seprate and purify, and 14-O-acetyl-4'-O-(1-isobutyloxyethyl) adriamycin a and b were obtained as follows:

Compound a: 40.4 mg.
Compound b: 51.7 mg.

(b) Deacetylation at C-14 position 40.4 mg of 14-O-acetyl-4'-O-(1-isobutyloxyethyl) adriamycin a obtained in (a) was dissolved in 4 ml of methanol, adding 2 ml of water and 0.36 ml of 1 N potassium carbonate aqueous solution and agitated for 20 min. at room temperature. The reaction mixture was neutralized with dry-ice, extracted with 60 ml of chloroform and then washed with 50 ml of 5% sodium chloride aqueous solution. The aqueous layer was further extracted twice with 20 ml of chloroform respectively, and the combined chloroform extracts were dried over anhydrous sodium sulfate and concentrated to dryness. 35.8 mg of the resulting residue was chromatographed by preparative thin-layer chromatography (Merck Art. 5744, 4 plates, CHCl$_3$:methanol=10:1) to obtain 12.5 mg of 4'-O-(1-isobutyloxyethyl) adriamycin a.

| | | |
|---|---|---|
| Melting point (°C.): | 180–185 (decomposition) | |
| Specific rotation (C = 0.1 in chloroform) $[\alpha]_D^{25}$: | +157° | |
| PMR (CDCl$_3$, ppm): | 0.93 (d, 6H) | CH(CH$_3$)$_2$ |
| | 1.32 (d, 3H) | C5'-CH$_3$ |
| | 1.38 (d, 3H) | C4'-OCHCH$_3$ |
| | 2.86 (d, 1H) | } C10-CH$_2$ |
| | 3.16 (d, 1H) | |
| | 3.66 (bs, 1H) | C4'-H |
| | 4.02 (s, 3H) | C4-OCH$_3$ |
| | 4.74 (s, 2H) | C14-CH$_2$ |
| | 4.88 (q, 1H) | C4'-OCHCH$_3$ |
| | 5.18 (bs, 1H) | C7-H |
| | 5.48 (bs, 1H) | C1'-H |
| | 7.25–7.92 (m-3H) | aromatic proton |

51.7 mg of 14-O-acetyl-4'-O-(1-isobutyloxyethyl) adriamycin b obtained in (a) was dissolved in 5 ml of methanol, adding 1.5 ml of water and 0.39 ml of 1 N potassium carbonate aqueous solution and agitated for 15 min. at room temperature. According to the method for compound a, 18.1 mg of 4'-O-(1-isobutyloxyethyl) adriamycin b was obtained.

| | | |
|---|---|---|
| Melting point (°C.): | 175–180 (decomposition) | |
| Specific rotation (C = 0.1 in chloroform) $[\alpha]_D^{25}$: | +191° | |
| PMR (CDCl$_3$, ppm): | 0.90 (d, 6H) | CH(CH$_3$)$_2$ |
| | 1.27 (d, 3H) | C5'-CH$_3$ |
| | 1.40 (d, 3H) | C4'-OCHCH$_3$ |
| | 2.84 (d, 1H) | } C10-CH$_2$ |
| | 3.16 (d, 1H) | |
| | 3.26 (t, 2H) | OCH$_2$CH |
| | 3.58 (bs, 1H) | C4'-H |
| | 4.01 (s, 3H) | C4-OCH$_3$ |
| | 4.60 (q, 1H) | C4'-OCHCH$_3$ |
| | 4.74 (s, 2H) | C14-CH$_2$ |
| | 5.18 (bs, 1H) | C7-H |
| | 5.48 (bs, 1H) | C1'-H |
| | 7.25–7.90 (m, 3H) | aromatic proton |

EXAMPLE 10

Process for producing 4'-O-(1-(6-methylheptyloxy) ethyl) adriamycin a and b (a) 150 mg of 14-O-acetyl adriamycin p-toluenesulfonate was dissolved in 2 ml of absolute DMSO and 4 ml of absolute dioxane, adding 1.6 ml of 6-methylheptyl vinyl ether and 0.396 ml of 0.1 N p-toluenesulfonic acid-dioxane solution under ice-cold conditions, and agitated for 45 min. at room temperature. According to the same method as that of (a) in Example 8, 14-O-acetyl-4'-O-(6-methylheptyloxyethyl) adriamycin a and b were obtained.

Compound a: 32.7 mg.
Compound b: 57.4 mg.

(b) Deacetylation 44.2 mg of 14-O-acetyl-4'-O-(1-(6-methylheptyloxy) ethyl) adriamycin b was dissolved in 5.8 ml of methanol and 1.3 ml of water, adding 0.39 ml of 1 N potassium carbonate solution to obtain a blue-violet color, and allowed to stand for 6 min. at room temperature. According to the same method as that of (b) in Example 8, 20.1 mg of 4'-O-(6-methylheptyloxy)ethyl adriamycin b was obtained. 13 mg of compound a was obtained in the same manner as mentioned above.

| Compound a | | |
|---|---|---|
| Melting point (°C.): | 143–147 | |
| Specific rotation (C = 0.1 in chloroform) $[\alpha]_D^{25}$: | +178° | |
| PMR (CDCl$_3$, ppm): | 1.32 (d, 3H) | C5'-CH$_3$ |
| | 1.38 (d, 3H) | C4'-OCHCH$_3$ |
| | 2.96 (d, 1H) | } C10-CH$_2$ |
| | 3.26 (d, 1H) | |
| | 4.06 (s, 3H) | C4-OCH$_3$ |
| | 4.75 (s, 2H) | C14-2H |
| | 4.90 (q, 1H) | C4'-OCHCH$_3$ |
| | 5.28 (bs, 1H) | C7-H |
| | 5.51 (bs, 1H) | C1'-H |
| | 7.31–8.03 (m, 3H) | aromatic proton |

| Compound b | | |
|---|---|---|
| Melting point (°C.): | 145–150 | |
| Specific rotation (C = 0.1 in chloroform) $[\alpha]_D^{25}$: | +183° | |
| PMR (CDCl$_3$, ppm): | 1.27 (d, 3H) | C5'-CH$_3$ |
| | 1.40 (d, 3H) | C4'-OCHCH$_3$ |
| | 2.93 (d, 1H) | } C10-CH$_2$ |
| | 3.25 (d, 1H) | |
| | 4.06 (s, 3H) | C4-OCH$_3$ |
| | 4.61 (q, 1H) | C4'-OCHCH$_3$ |
| | 4.75 (s, 2H) | C14-CH$_2$ |
| | 5.25 (bs, 1H) | C7-H |
| | 5.52 (bs, 1H) | C1'-H |
| | 7.30–8.00 (m, 3H) | aromatic proton |

EXAMPLE 11

Process for producing 4'-O-(1-cyclohexyloxyethyl) adriamycin a and b (a) 210 mg of p-toluenesulfonate of 14-O-acetyl adriamycin was dissolved in 4.2 ml of anhydrous dioxane and 2.1 ml of anhydrous dimethyl sulfoxide, adding 0.84 ml of cyclohexyl vinyl ether and 0.417 ml of 0.1 N p-toluenesulfonic acid-dioxane solution, and allowed to react while agitating for 20 min. at room temperature. Subsequently, the reaction mixture was followed by the same treatment as that mentioned in Example 8 (a) to obtain 56.9 mg of 14-O-acetyl-4'-O-cyclohexyloxyethyl adriamycin a and 60.7 mg of 14-O-acetyl-4'-O-cyclohexyloxyethyl adriamycin b.

(b) Deacetylation at the C-14 position 56.9 mg of 14-O-acetyl-4'-O-cyclohexyloxyethyl adriamycin a and 60.7 mg of 14-O-acetyl-4'-cyclohexyloxyethyl adriamycin b respectively obtained in (a) were treated in the same manner as that mentioned in Example 8 (b) to obtain 20.7 mg of orange powder of 4'-O-cyclohexyloxyethyl adriamycin a and 24.2 mg of orange powder of 4'-O-cyclohexyloxyethyl adriamycin b respectively.

| Compound a | | |
|---|---|---|
| Melting point (°C.): | 175–182 (decomposition) | |
| Specific rotation (C = 0.1 in chloroform) $[\alpha]_D^{25}$: | +178° | |
| PMR (CDCl$_3$, ppm): | 1.32 (d, 3H) | C5'-CH$_3$ |
| | 1.38 (d, 3H) | C4'-OCHCH$_3$ |
| | 2.92 (d, 1H) | ⎫ |
| | | ⎬ C10-CH$_2$ |
| | 3.23 (d, 1H) | ⎭ |
| | 4.05 (s, 3H) | 4-OCH$_3$ |
| | 4.76 (s, 2H) | C14-CH$_2$ |
| | 4.97 (q, 1H) | C4'-OCHCH$_3$ |
| | 5.23 (bs, 1H) | C7-H |
| | 5.49 (bs, 1H) | C1'-H |
| | 7.30–8.00 (m, 3H) | aromatic proton |

| Compound b | | |
|---|---|---|
| Melting point (°C.): | 177–181 (decomposition) | |
| Specific rotation (C = 0.1 in chloroform) $[\alpha]_D^{25}$: | +172° | |
| PMR (CDCl$_3$, ppm): | 1.26 (d, 3H) | C5'-CH$_3$ |
| | 1.40 (d, 3H) | C4'-OCHCH$_3$ |
| | 2.87 (d, 1H) | ⎫ |
| | | ⎬ C10-CH$_2$ |
| | 3.18 (d, 1H) | ⎭ |
| | 4.02 (s, 3H) | 4-OCH$_3$ |
| | 4.68 (q, 1H) | C4'-OCHCH$_3$ |
| | 4.74 (s, 2H) | C14-CH$_2$ |
| | 5.19 (bs, 1H) | C7-H |
| | 5.49 (bs, 1H) | C1'-H |
| | 7.26–7.94 (m, 3H) | aromatic proton |

EXAMPLE 12

Process for producing 4'-O-(tetrahydrofuranyl) daunomycin 56 mg (0.1 mmoles) of daunomycin hydrochloride was dissolved in dry dimethylformamide, adding 0.1 ml of dihydrofuran and a small amount of p-toluenesulfonic acid as a catalyst, and allowed to stand for 8 hours at room temperature (4'-O-tetrahydrofuranylation). The reaction mixture was poured into 200 ml of water, adding sodium hydrogen carbonate to neutralize, and extracted with chloroform. The chloroform layer was dried over anhydrous sodium sulfate and concentrated to dryness to obtain red materials. Two bands of the product having Rf 0.29 and 0.31 were detected by preparative thin-layer chromatography using silica gel (Merck Co.) and a solvent system of chloroform:methanol (9:1), but these bands could not be completely separated from each other.

The bands corresponding to the product were scratched out from silica gel plate and eluted with a chloroform-methanol mixture (1:1), and the eluate was concentrated under reduced pressure to obtain 12.4 mg of 4'-O-(tetrahydrofuranyl) daunomycin as red powder.

Yield 21%.

Melting point (°C.): 201–204 (decomposition).

PMR (CDCl$_3$, ppm): 1.29(6'-H), 1.70–2.30(furan-3,4-H), 2.44(14-H), 4.11(4-H), 5.28(1'-H), 5.43(furan, anomeric), 5.54(7-H), 7.33–8.11(1-H–3-H).

EXAMPLE 13

Process for producing 4'-O-(6-acetoxymethyltetrahydropyranyl) daunomycin 112 mg (0.2 mmoles) of daunomycin hydrochloride was dissolved in 2.0 ml of dry dimethylformamide, adding 15 mg of p-toluenesulfonic acid and 0.3 ml of 2-acetoxymethyl-3,4-dihydro-2H-pyran and allowed to stand over night at room temperature (4'-O-(6-acetoxymethyltetrahydropyranylation). The reaction mixture was poured into 20 ml of 1% sodium hydrogen carbonate aqueous solution and extracted with 30 ml of chloroform.

The aqueous layer was extracted twice with 10 ml of chloroform respectively. The combined chloroform layer was washed four times with 10 ml of water, dried over anhydrous sodium sulfate and concentrated under reduced pressure to obtain the crude product. The product was developed on a preparative thin-layer chromatogram (2 mm thickness, 20×20 cm, one plate) using a solvent system of chloroform-methanol (9:1), and the band corresponding to the product having Rf 0.47 was scratched out from silica gel thin-layer and re-extracted with a chloroform-methanol mixture (1:1). The resulting red extract was concentrated to dryness and 55.3 mg of 4'-O-(6-acetoxymethyltetrahydropyranyl) daunomycin was obtained as red powder.

Yield 40%.

Melting point (°C.): 198–201.

PMR (CDCl$_3$, ppm): 1.21–1.42(6'-H), 2.07–2.11(OAc), 2.43(14-H), 4.10(4-OMe), 5.53(7-H), 7.29–8.06(1-H--3-H).

EXAMPLE 14

Process for producing 4'-O-(6-methoxytetrahydropyranyl) daunomycin a and b 112 mg (0.2 mmoles) of daunomycin hydrochloride was dissolved in 3.0 ml of dry dimethylformamide, adding 0.15 ml of 2-methoxy-3,4-dihydro-2H-pyran and 10 mg of p-toluenesulfonic acid and allowed to stand overnight at room temperature (4'-O-(6-methoxytetrahydropyranylation). The reaction mixture was poured into 20 ml of water, adjusting the pH at 8.0 with sodium hydrogen carbonate and extracted four times with 10 ml of chloroform respectively. The chloroform extracts were combined, dried over anhydrous sodium sulfate and concentrated to dryness to obtain red residue. The residue was further purified by preparative thin-layer chromatography using silica gel (Merck Co. 2 mm thickness, 20×20 cm, one plate) and a solvent system of chloroform-methanol (9:1). A band of Rf 0.38 was scratched out from the silica gel plate, and re-extrcted with a chloroform-methanol mixture (1:1). The resulting red extract was concentrated under reduced pressure to obtain 23.1 mg of compound a as red powder.

Yield 18%.
Melting point (°C.): 189–191.
PMR (CDCl$_3$), ppm: 1.29(6'-H), 2.40(3-H), 3.45(5'-OMe), 4.09(4-OMe), 4.83(1'-H), 5.30(1'-H), 5.58(7-H), 7.28–8.08(1-H–3-H).

19.4 mg of compound b was obtained as red powder according to the same method as that of compound a.
Yield 15%.
Melting point (°C.): 198–199.
PMR (CDCl$_3$, ppm): 1.39(6'-H), 2.44(14-H), 3.46(pyran-OMe), 4.11(4-H), 4.89(pyran, anomeric), 5.22(1'-H), 5.53(7-H), 7.28–8.14(1-H–3-H).

EXAMPLE 15

Process for producing 4'-O-(6-carbomethoxytetrahydropyranyl) daunomycin 112 mg (0.2 mmoles) of daunomycin hydrochloride was dissolved in 3.0 ml of dry dimethylformamide, adding 0.1 ml of 2-carbomethoxy-3,4-dihydro-2H-pyran and 34 mg (0.2 mmoles) of p-toluenesulfonic acid, and allowed to stand for 10 hours at room temperature in the dark (4'-O-6-carbomethoxytetrahydropyranylation). The reaction mixture was poured into 20 ml of water, adjusting the pH at 8 with sodium hydrogen carbonate and extracted four times with 10 ml of chloroform respectively. The chloroform extracts were combined, washed twice with water and dried over anhydrous sodium sulfate. The chloroform extract was concentrated under reduced pressure, and the resulting residue was purified by preparative thin-layer chromatography using a silica gel plate (Merck Co.) and a solvent system of chloroform-methanol (9:1). New products were detected between 0.35 and 0.37 of Rf values on the TLC as a mixture of 4 components, and they could not be separated completely. The corresponding bands on the TLC were scratched out from the silica gel plate and extracted with a chloroform-methanol mixture (1:1). The extract was concentrated to dryness to obtain 25.9 mg of red powder.

Yield 19%.
Melting point (°C.): 190–193.
PMR (CDCl$_3$, ppm): 1.23–1.40(6'-H), 2.43(14-H), 3.78(COOCH$_3$), 4.09(4-OMe), 4.74, 5.07(pyran, anomeric), 5.31(1'-H), 5.54(7-H), 7.30–8.06(1-H–3-H).

EXAMPLE 16

Process for producing 4'-O-(1-ethyloxyethyl) daunomycin a and b 112 mg (0.2 mmoles) of daunomycin hydrochloride was dissolved in 3 ml of dry dimethylformamide, 0.1 ml of ethyl vinyl ether and 2 mg of p-toluenesulfonic acid and allowed to stand for 10 hours at room temperature (1-ethyloxyethylation). New spots of the product were observed at Rf 0.31 and 0.34 on the silica gel thin-layer chromatogram (solvent system, chloroform-methanol=9:1). The reaction mixture was poured into 20 ml of water, adjusting the pH at 8 with sodium hydrogen carbonate, and extracted with 30 ml of chloroform. The chloroform layer was dried and concentrated under reduced pressure. The resulting red residue was purified by preparative thin-layer chromatography using silica gel (Merck Co. thickness 2 mm, 20×20 cm, one plate) and a solvent system of chloroform-methanol (15:1). The band corresponding to Rf 0.31 was scratched out, and extracted with a chloroform-methanol mixture (1:1). The red extract was concentrated to dryness to obtain 33.0 mg of red compound a.

Yield 27%.
Melting point (°C.): 208–210.
PMR (CDCl$_3$, ppm): 1.76, 3.59(1'-OEt), 1.39(2'-H), 1.79(8-H), 2.41(14-H), 4.07 (4-OMe), 4.64(1'-H), 5.25(1'-H), 5.51(7-H), 7.25–8.07(1-H–3-H).

The band corresponding to Rf 0.34 was also treated according to the same method as that mentioned above, and 31.8 mg of compound b was obtained as red powder.

Yield 26%.
Melting point (°C.): 200–204.
PMR (CDCl$_3$, ppm): 1.20, 3.64(1'-OEt), 1.40(2'-H), 2.41(14-H), 4.09(4-H), 4.94 (1'-H), 5.26(1'-H), 5.50(7-H), 7.26—8.07(1-H–3-H).

EXAMPLE 17

Process for producing 4'-O-(1-isobutyloxyethyl) daunomycin a and b 60 mg (0.106 mmoles) of daunomycin hydrochloride was dissolved in 12 ml of absolute THF and 1.5 ml of absolute DMSO, adding 1.2 ml of 2-isobutyl vinyl ether and 0.21 ml of 0.1 N p-toluenesulfonic acid-THF solution, and agitated for three hours at room temperature. The reaction mixture was dissolved in 100 ml of ethylacetate, washed with 100 ml of 5% sodium chloride aqueous solution containing 0.1 N sodium hydrogen carbonate, and further washed with 5% sodium chloride aqueous solution (100 ml×2). The solvent layer was dried over anhydrous sodium sulfate and concentrated under reduced pressure. The resulting oily substance was treated in the same manner as that mentioned in Example 16 to obtain 16.0 mg of 4'-O-(1-isobutyloxyethyl) daunomycin a and 19.1 mg of 4'-O-(1-isobutyloxyethyl) daunomycin b.

| Compound a | | |
|---|---|---|
| Melting point (°C.): | 143–148 | |
| Specific rotation (C = 0.1 in chloroform) $[\alpha]_D^{25}$: | +190° | |
| PMR (CDCl$_3$, ppm): | 0.92 (d, 6H) | —CH(CH$_3$)$_2$ |
| | 1.33 (d, 3H) | C5'—CH$_3$ |
| | 1.37 (d, 3H) | C4'—OCHCH$_3$ |
| | 2.41 (s, 3H) | C13—CH$_3$ |
| | 2.90 (d, 1H) | ⎫ C10-CH$_2$ |
| | 3.22 (d, 1H) | ⎭ |
| | 3.27 (t, 2H) | OCH$_2$CH |
| | 3.62 (bs, 1H) | C4'-H |
| | 4.07 (s, 3H) | C4-OCH$_3$ |
| | 4.89 (q, 1H) | C4'-OCHCH$_3$ |
| | 5.28 (bs, 1H) | C7-H |
| | 5.52 (bs, 1H) | C1'-H |
| | 7.31–8.06 (m, 3H) | aromatic proton |

| Compound b | | |
|---|---|---|
| Melting point (°C.): | 141–146 | |
| Specific rotation (C = 0.1 in chloroform) $[\alpha]_D^{25}$: | +185° | |
| PMR (CDCl$_3$, ppm): | 0.90 (d, 6H) | CH(CH$_3$)$_2$ |
| | 1.25 (d, 3H) | C5'-CH$_3$ |
| | 1.39 (d, 3H) | C4'-OCHCH$_3$ |

-continued

| Compound b | | |
|---|---|---|
| 2.40 (s, 3H) | | C13-CH$_3$ |
| 2.89 (d, 1H) | ⎫ | |
| 3.22 (d, 1H) | ⎬ | C10-CH$_2$ |
| 3.26 (t, 2H) | | OCH$_2$CH |
| 3.54 (bs, 1H) | | C4'-H |
| 4.06 (s, 3H) | | C4-OCH$_3$ |
| 4.61 (q, 1H) | | C4'-OCHCH$_3$ |
| 5.27 (bs, 1H) | | C7-H |
| 5.52 (bs, 1H) | | C1'-H |
| 7.31–8.04 (m, 3H) | | aromatic proton |

EXAMPLE 18

Process for producing 4'-O-(1-butyloxyethyl) daunomycin a and b 100 mg (0.177 mmoles) of daunomycin hydrochloride was dissolved in a mixture of 10 ml of absolute THF and 2 ml of absolute DMSO, adding 3 ml of n-butyl vinyl ether and 0.88 ml (0.088 mmoles) of 0.1 N p-toluenesulfonic acid-THF solution, and agitated for two hours at room temperature. According to the method of Example 17, 27.1 mg of 4'-O-(1-butyloxyethyl) daunomycin a and 34.8 mg of 4'-O-(1-butyloxyethyl) daunomycin b were separated.

| Compound a | | |
|---|---|---|
| Melting point (°C.): | 141–145 | |
| Specific rotation (C = 0.1 in chloroform) | | |
| $[\alpha]_D^{25}$: | +167° | |
| PMR (CDCl$_3$, ppm): | 0.91 (t, 3H) | —CH$_2$CH$_3$ |
| | 1.32 (d, 3H) | C5'-CH$_3$ |
| | 1.37 (d, 3H) | C4'-OCHCH$_3$ |
| | 2.41 (s, 3H) | C13-CH$_3$ |
| | 2.92 (d, 1H) | ⎫ |
| | | ⎬ C10-CH$_2$ |
| | 3.24 (d, 1H) | ⎭ |
| | 3.54 (m, 3H) | C4'-H, OCH$_2$— |
| | 4.07 (s, 3H) | C4-OCH$_3$ |
| | 4.91 (q, 1H) | C4'-OCHCH$_3$ |
| | 5.27 (bs, 1H) | C7-H |
| | 5.52 (bs, 1H) | C1'-H |
| | 7.31–8.06 (m, 3H) | aromatic proton |

| Compound b | | |
|---|---|---|
| Melting point (°C.): | 138–142 | |
| Specific rotation (C = 0.1 in chloroform) | | |
| $[\alpha]_D^{25}$: | +207° | |
| PMR (CDCl$_3$, ppm): | 0.89 (t, 3H) | —CH$_2$CH$_3$ |
| | 1.27 (d, 3H) | C5'-CH$_3$ |
| | 1.39 (d, 3H) | C4'-OCHCH$_3$ |
| | 2.40 (s, 3H) | C13-CH$_3$ |
| | 2.86 (d, 1H) | ⎫ |
| | | ⎬ C10-CH$_2$ |
| | 3.20 (d, 1H) | ⎭ |
| | 3.52 (m, 3H) | C4'-H, OCH$_2$— |
| | 4.06 (s, 3H) | C4-OCH$_3$ |
| | 4.61 (q, 1H) | C4'-OCHCH$_3$ |
| | 5.25 (bs, 1H) | C7-H |
| | 5.51 (bs, 1H) | C1'-H |
| | 7.30–8.01 (m, 3H) | aromatic proton |

EXAMPLE 19

Process for Producing 4'-O-Tetrahydropyranyl Daunomycin (4'-O-PDa and 4'-O-PDb)

To a solution of daunomycin hydrochloride (60 mg.) in 5 ml of anhydrous dimethylformamide was added 1 ml. of 3,4-dihydro-2H-pyrane and a catalytic amount of p-toluenesulfonic acid. After being allowed to stand overnight at room temperature in the dark, the reaction mixture was added to 20 ml. of 0.1 N sodium hydrogen carbonate aqueous solution and extracted with chloroform (10 ml.×4). After the chloroform-extract was extracted with 1% acetic acid solution (10 ml.×10), the resulting acidic aqueous layer was neutralized with sodium hydrogen carbonate and then re-extracted with chloroform (20 ml.×10). The chloroform layer was dried over anhydrous sodium sulfate and concentrated to dryness. The 44 mg. of residue thus obtained was applied to preparative silica gel thin-layer chromatography (Merck Co. 60F$_{254}$) and developed by a chloroform-methanol mixture (10:1) (v/v).

Silica gel bands corresponding to R$_f$ 0.46 and 0.65 were scratched out from the thin-layer, eluted with the chloroform-methanol mixture (10:1) (v/v) and concentrated to dryness. Each residue was dissolved in methylene chloride, frozen by addition of t-butanol under cooling and dried under reduced pressure. There were obtained 10.1 mg. of reddish brown solid of 4'-O-PDa and 10.3 mg. of red solid of 4'-O-PDb from the R$_f$ 0.46 and 0.65 fractions, respectively.

4'-O-PDa and 4'-O-PDb are diastereomers of 4'-O-tetrahydropyranyl daunomycin, and their physicochemical properties are as shown in Table 1.

EXAMPLE 20

Process for Producing 4',14-O-bis(Tetrahydropyranyl)adriamycin (4',14-di-O-PAa and 4',14-di-O-PAb) and 14-O-Tetrahydropyranyl Adriamycin (14-O-PA) from Adriamycin To a solution of adriamycin hydrochloride (130 mg.) in 10 ml. of anhydrous dimethylformamide was added 2 ml. of 3,4-dihydro-2H-pyrane and a catalytic amount of p-toluenesulfonic acid. After being allowed to stand for 48 hours at room temperature in the dark, the reaction mixture was added to 20 ml. of 0.1 N sodium hydrogen carbonate aqueous solution and extracted with ethyl acetate (20 ml.×5). After extracting the ethyl acetate layer with 1% acetic acid solution (40 ml.×4), the acidic aqueous layer was neutralized with sodium hydrogen carbonate and extracted with chloroform (20 ml.×10). The chloroform layer was dried over anhydrous sodium sulfate and concentrated to dryness. The 160 mg. of resulting solid was developed and purified by a preparative silica gel thin-layer chromatography using a chloroform-methanol mixture (10:1) (v/v). The bands of R$_f$ 0.12 and 0.55 were scratched out from the thin-layer and purified according to the method of Example 19.

There were obtained 35 mg. of red solid of 14-O-PA, 16 mg. of red solid of 4',14-di-O-PAa and 14 mg. of red solid of 4',14-di-O-PAb from the R$_f$ 0.12, 0.55 and 0.73 fractions, respectively.

4',14-di-O-PAa and 4',14-di-O-PAb are diastereomers of 4',14-bis(O-tetrahydropyranyl) adriamycin and their physicochemical properties are as shown in Table 1.

EXAMPLE 21

Process for Producing 4',14-bis(O-Tetrahydropyranyl)adriamycin from 14-O-Tetrahydropyranyl Adriamycin To a solution of 35 mg. of 14-O-PA in 2 ml. of anhydrous dimethylformamide, there was added 0.5 ml. of 3,4-dihydro-2H-pyrane and a catalytic amount of p-toluenesulfonic acid. After being allowed to stand for 40 hours at room temperature in the dark, the reaction mixture was added to 10 ml. of 0.02 N sodium hydrogen carbonate aqueous solution and extracted with ethyl acetate (5 ml.×4). After extracting the ethyl acetate layer with 1% acetic acid solution (10 ml.×3), the acidic aqueous layer was neutralized with sodium hydrogen carbonate and extracted with chloroform (10 ml.×5). The chloroform layer was dried over anhydrous sodium sulfate and concentrated to dryness.

The resulting residue was chromatographed using a silica gel thin-layer according to Example 20, and 8.4 mg. of red solid of 4',14-di-O-PAa and 8.1 mg. of red solid of 4',14-di-O-PAb were obtained from the $R_f$ 0.55 and 0.73 fractions, respectively. Their physicochemical properties coincided with those of the compounds obtained in Example 20.

EXAMPLE 22

Process for Producing 4'-O-Tetrahydropyranyl Adriamycin from 4',14-bis(O-Tetrahydropyranyl)adriamycin (a) 4',14-di-O-PAa (12.4 mg.) was dissolved in 1.5 ml. of 10% acetic acid solution and allowed to stand for 4.5 hours at room temperature in the dark. The reaction mixture was added to 10 ml. of water, neutralized with sodium hydrogen carbonate powder, and extracted with chloroform (15 ml.×2).

The chloroform layer was dried over anhydrous sodium sulfate and concentrated to dryness. The 11 mg. of resulting residue was purified by a silica gel thin-layer chromatography as described above using a chloroform-methanol mixture (10:1) (v/v). The main band at $R_f$ 0.32 was scratched out and eluted with the chloroform-methanol mixture (10:1) (v/v). The eluate was concentrated to dryness. The residue was dissolved in methylene chloride, adding t-butanol under cooling to freeze, and dried under reduced pressure. There was obtained 7 mg. of red solid of 4'-O-PAa and its physicochemical properties are shown in Table 1.

(b) 4',14-di-O-PAb (16 mg.) was dissolved in 5 ml. of 0.005 N p-toluenesulfonic acid-methanol solution and allowed to stand for 1 hour at room temperature in the dark. The reaction mixture was neutralized with 10 ml. of 0.01 N sodium hydrogen carbonate aqueous solution and extracted with chloroform (10 ml.×4). The chloroform layer was dried over anhydrous sodium sulfate and treated as shown in (a). There was obtained 7.2 mg. of red solid of 4'-O-PAb which shows $R_f$ 0.49 on a silica gel thin-layer under the conditions as described above. Its physicochemical properties are shown in Table 1.

4'-O-PAa and 4'-O-PAb are diastereomers of 4'-O-tetrahydropyranyl adriamycin.

EXAMPLE 23

Salt Formation

Illustrative of the procedures which may be used to prepare acid addition salts, the free base of 4'-O-PDa, 4'-O-PDb, 4',14-di-O-PAa, 4',14-di-O-PAb, 14-O-PA, 4'-O-PAa or 4'-O-PAb may be dissolved in ethyl acetate and about one equivalent of HCl added. On lyophilization, the appropriate hydrochloride salt is obtained.

The acid addition salts of the other etherified anthracycline glycosides of formula I may be prepared in a similar manner by using the appropriate organic or inorganic acid and the appropriate free base starting material.

We claim:

1. An anthracycline glycoside of the formula

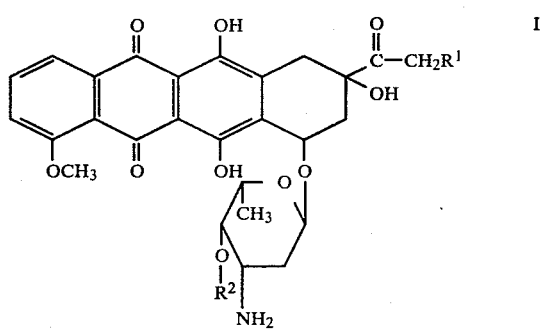

wherein $R^1$ represents hydrogen, hydroxyl, tetrahydropyranyloxy, $C_2$-$C_7$ alkanoyloxy or phenylacetyloxy and $R^2$ represents hydrogen, $C_1$-$C_8$ alkyloxyethyl, cyclohexyloxyethyl, tetrahydrofuranyl, tetrahydropyranyl, 6-methoxytetrahydropyranyl, 6-carbomethoxytetrahydropyranyl or 6-acetoxymethyltetrahydropyranyl, with the provisos that (1) when $R^1$ is hydrogen or hydroxyl, $R^2$ is not hydrogen and (2) when $R^1$ is tetrahydropyranyloxy, $R^2$ is hydrogen or tetrahydropyranyl, or a nontoxic acid addition salt thereof.

2. An anthracycline glycoside of the formula

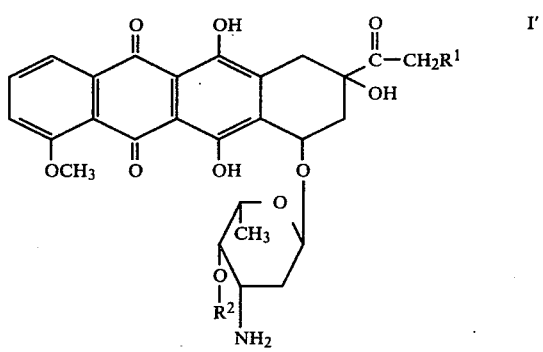

wherein $R^1$ represents a hydrogen atom, a hydroxyl group or a tetrahydropyranyloxy group and $R^2$ represents a hydrogen atom or a tetrahydropyranyl group, providing that when $R^1$ is a hydrogen atom or a hydroxyl group, $R^2$ is a tetrahydropyranyl group, or a nontoxic acid addition salt thereof.

3. An anthracycline glycoside of the formula

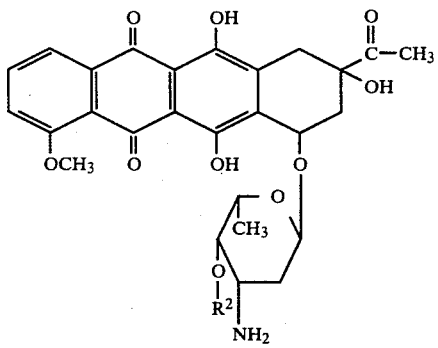

wherein R² is a tetrahydropyranyl group, or a nontoxic acid addition salt thereof.

4. The compound according to claim 3 which is 4'-O-tetrahydropyranyl daunomycin (isomer a), or a nontoxic acid addition salt thereof.

5. The compound according to claim 3 which is 4'-O-tetrahydropyranyl daunomycin (isomer b), or a nontoxic acid addition salt thereof.

6. The anthracycline glycoside of the formula

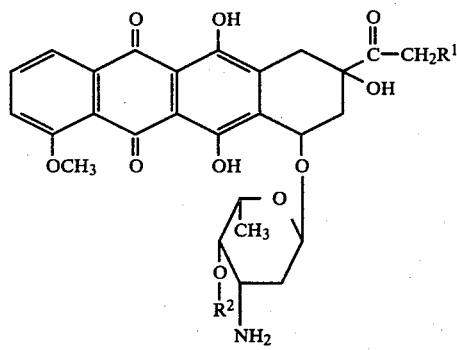

wherein R¹ is a tetrahydropyranyloxy group and R² is hydrogen, or a nontoxic acid addition salt thereof.

7. An anthracycline glycoside of the formula

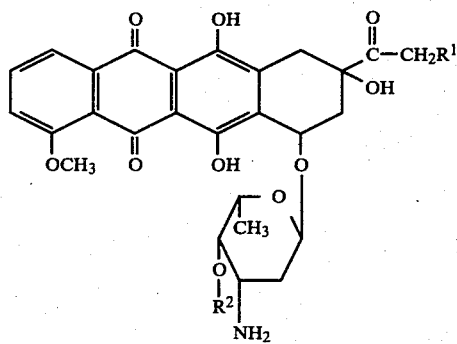

wherein R¹ is tetrahydropyranyloxy and R² is tetrahydropyranyl, or a nontoxic acid addition salt thereof.

8. The compound according to claim 7 which is 4',14-bis(O-tetrahydropyranyl)adriamycin (isomer a), or a nontoxic acid addition salt thereof.

9. The compound according to claim 7 which is 4',14-bis(O-tetrahydropyranyl)adriamycin (isomer b), or a nontoxic acid addition salt thereof.

10. An anthracycline glycoside of the formula

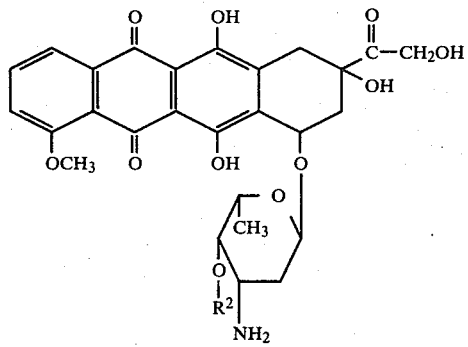

wherein R² is a tetrahydropyranyl group, or a nontoxic acid addition salt thereof.

11. The compound according to claim 10 which is 4'-O-tetrahydropyranyl adriamycin (isomer a), or a nontoxic acid addition salt thereof.

12. The compound according to claim 10 which is 4'-O-tetrahydropyranyl adriamycin (isomer b), or a nontoxic acid addition salt thereof.

13. An anthracycline glycoside of the formula

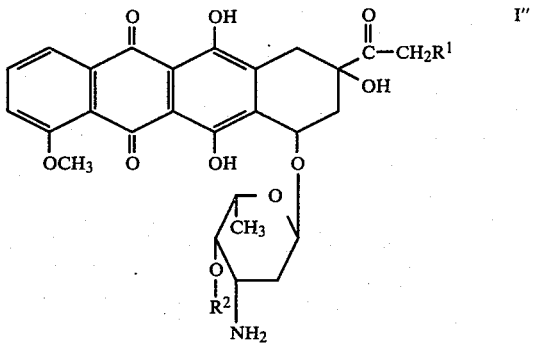

wherein R¹ is a hydrogen atom, a hydroxyl group, an alkoanoyloxy group having from 2 to 7 carbon atoms inclusive or a phenylacetyloxy group and R² is alkyloxyethyl in which the alkyl portion has from 1 to 8 carbon atoms inclusive, cyclohexyloxyethyl, tetrahydrofuranyl, tetrahydropyranyl, 6-methoxytetrahydropyranyl, 6-carbomethoxytetrahydropyranyl or 6-acetoxymethyltetrahydropyranyl, with the proviso that when R¹ is hydrogen or hydroxyl, R² is not tetrahydropyranyl, or a nontoxic acid addition salt thereof.

14. An anthracycline glycoside according to claim 13 wherein R¹ is acetyloxy, isobutyloyloxy or phenylacetyloxy and R² is alkyloxyethyl in which the alkyl portion has from 1 to 8 carbon atoms inclusive, cyclohexyloxyethyl, tetrahydrofuranyl, tetrahydropyranyl, 6-methoxytetrahydropyranyl, 6-carbomethoxytetrahydropyranyl or 6-acetoxymethyltetrahydropyranyl, or a nontoxic acid addition salt thereof.

15. An anthracycline glycoside according to claim 13 wherein R¹ is hydrogen or hydroxyl and R² is alkyloxyethyl in which the alkyl portion has from 1 to 8 carbon atoms inclusive, cyclohexyloxyethyl, tetrahydrofuranyl, 6-methoxytetrahydropyranyl, or 6-acetoxymethyltetrahydropyranyl, or a nonotoxic acid addition salt thereof.

16. The compound of claim 13 which is 14-O-acetyl-4'-O-tetrahydropyranyl adriamycin (isomer a), or a nontoxic acid addition salt thereof.

17. The compound of claim 13 which is 14-O-acetyl-4'-O-tetrahydropyranyl adriamycin (isomer b), or a nontoxic acid addition salt thereof.

18. The compound of claim 13 which is 14-O-isobutyloyl-4'-O-tetrahydropyranyl adriamycin (isomer a), or a nontoxic acid addition salt thereof.

19. The compound of claim 13 which is 14-O-isobutyloyl-4'-O-tetrahydropyranyl adriamycin (isomer b), or a nontoxic acid addition salt thereof.

20. The compound of claim 13 which is 14-O-phenylacetyl-4'-O-tetrahydropyranyl adriamycin (isomer a), or a nontoxic acid addition salt thereof.

21. The compound of claim 13 which is 14-O-phenylacetyl-4'-O-tetrahydropyranyl adriamycin (isomber b), or a nontoxic acid addition salt thereof.

22. The compound of claim 13 which is 14-O-acetyl-4'-O-tetrahydrofuranyl adriamycin, or a nontoxic acid addition salt thereof.

23. The compound of claim 13 which is 4'-O-tetrahydrofuranyl adriamycin, or a nontoxic acid addition salt thereof.

24. The compound of claim 13 which is 4'-O-tetrahydrofuranyl adriamycin (isomer a), or a nontoxic acid addition salt thereof.

25. The compound of claim 13 which is 4'-O-tetrahydrofuranyl adriamycin (isomer b), or a nontoxic acid addition salt thereof.

26. The compound of claim 13 which is 14-O-phenylacetyl-4'-O-(6-acetoxymethyltetrahydropyranyl)adriamycin, or a nonotoxic acid addition salt thereof.

27. The compound of claim 13 which is 4'-O-(6-acetoxymethyltetrahydropyranyl)adriamycin, or a nontoxic acid addition salt thereof.

28. The compound of claim 13 which is 14-O-phenylacetyl-4'-O-(1-ethyloxyethyl)adriamycin, or a nontoxic acid addition salt thereof.

29. The compound of claim 13 which is 4'-O-(1-ethyloxyethyl)adriamycin (isomer a), or a nontoxic acid addition salt thereof.

30. The compound of claim 13 which is 4'-O-(1-ethyloxyethyl)adriamycin (isomer b), or a nontoxic acid addition salt thereof.

31. The compound of claim 13 which is 14-O-acetyl-4'-O-(1-butyloxyethyl)adriamycin (isomer a), or a nontoxic acid addition salt thereof.

32. The compound of claim 13 which is 14-O-acetyl-4'-O-(1-butyloxyethyl)adriamycin (isomer b), or a nontoxic acid addition salt thereof.

33. The compound of claim 13 which is 4'-O-(1-butyloxyethyl)adriamycin (isomer a), or a nontoxic acid addition salt thereof.

34. The compound of claim 13 which is 4'-O-(1-butyloxyethyl)adriamycin (isomer b), or a nontoxic acid addition salt thereof.

35. The compound of claim 13 which is 14-O-acetyl-4'-O-(1-isobutyloxyethyl)adriamycin (isomer a), or a nontoxic acid addition salt thereof.

36. The compound of claim 13 which is 14-O-acetyl-4'-O-(1-isobutyloxyethyl)adriamycin (isomer b), or a nontoxic acid addition salt thereof.

37. The compound of claim 13 which is 4'-O-(1-isobutyloxyethyl)adriamycin (isomer a), or a nonotoxic acid addition salt thereof.

38. The compound of claim 13 which is 4'-O-(1-isobutyloxyethyl)adriamycin (isomer b), or a nontoxic acid addition salt thereof.

39. The compound of claim 13 which is 14-O-acetyl-4'-O-(6-methylheptyloxyethyl)adriamycin (isomer a), or a nontoxic acid addition salt thereof.

40. The compound of claim 13 which is 14-O-acetyl-4'-O-(6-methylheptyloxyethyl)adriamycin (isomer b), or a nontoxic acid addition salt thereof.

41. The compound of claim 13 which is 4'-O-(6-methylheptyloxyethyl)adriamycin (isomer a), or a nontoxic acid addition salt thereof.

42. The compound of claim 13 which is 4'-O-(6-methylheptyloxyethyl)adriamycin (isomer b), or a nontoxic acid addition salt thereof.

43. The compound of claim 13 which is 14-O-acetyl-4'-O-cyclohexyloxyethyl adriamycin (isomer a), or a nontoxic acid addition salt thereof.

44. The compound of claim 13 which is 14-O-acetyl-4'-O-cyclohexyloxyethyl adriamycin (isomer b), or a nontoxic acid addition salt thereof.

45. The compound of claim 13 which is 4'-O-cyclohexyloxyethyl adriamycin (isomer a), or a nontoxic acid addition salt thereof.

46. The compound of claim 13 which is 4'-O-cyclohexyloxyethyl adriamycin (isomer b), or a nontoxic acid addition salt thereof.

47. The compound of claim 13 which is 4'-O-(tetrahydrofuranyl)daunomycin, or a nontoxic acid addition salt thereof.

48. The compound of claim 13 which is 4'-O-(6-acetoxymethyltetrahydropyranyl)daunomycin, or a nontoxic acid addition salt thereof.

49. The compound of claim 13 which is 4'-O-(6-methoxytetrahydropyranyl)daunomycin (isomer a), or a nontoxic acid addition salt thereof.

50. The compound of claim 13 which is 4'-O-(6-methoxytetrahydropyranyl)daunomycin (isomber b), or a nontoxic acid addition salt thereof.

51. The compound of claim 13 which is 4'-O-(6-carbomethoxytetrahydropyranyl)daunomycin, or a nonotoxic acid addition salt thereof.

52. The compound of claim 13 which is 4'-O-(1-ethyloxyethyl)daunomycin (isomer a), or a nontoxic acid addition salt thereof.

53. The compound of claim 13 which is 4'-O-(1-ethyloxyethyl)daunomycin (isomer b), or a nontoxic acid addition salt thereof.

54. The compound of claim 13 which is 4'-O-(1-isobutyloxyethyl)daunomycin (isomer a), or a nontoxic acid addition salt thereof.

55. The compound of claim 13 which is 4'-O-(1-isobutyloxyethyl)daunomycin (isomer b), or a nontoxic acid addition salt thereof.

56. The compound of claim 13 which is 4'-O-(1-butyloxyethyl)daunomycin (isomer a), or a nontoxic acid addition salt thereof.

57. The compound of claim 13 which is 4'-O-(1-butyloxyethyl)daunomycin (isomer b), or a nontoxic acid addition salt thereof.

58. An anthracycline glycoside of the formula

59. An anthracycline glycoside of the formula

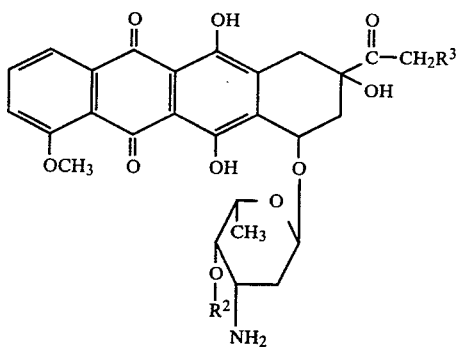

wherein R³ is phenylacetyloxy or alkanoyloxy having from 2 to 7 carbon atoms inclusive and R² is alkyloxyethyl in which the alkyl portion has from 1 to 8 carbon atoms inclusive, cyclohexyloxyethyl, tetrahydrofuranyl, tetrahydropyranyl, 6-methoxytetrahydropyranyl, 6-carbomethoxytetrahydropyranyl or 6-acetoxymethyltetrahydropyranyl, or a nontoxic acid addition salt thereof.

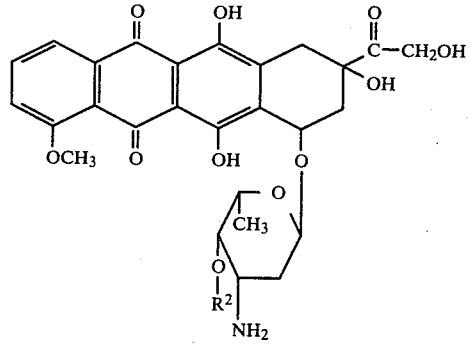

wherein R² is alkyloxyethyl in which the alkyl portion has from 1 to 8 carbon atoms inclusive, cyclohexyloxyethyl, tetrahydrofuranyl, 6-methoxytetrahydropyranyl, 6-methoxytetrahydropyranyl, 6-carbomethoxytetrahydropyranyl or 6-acetoxymethyltetrahydropyranyl, or a nontoxic acid addition salt thereof.

60. An anthracycline glycoside of the formula

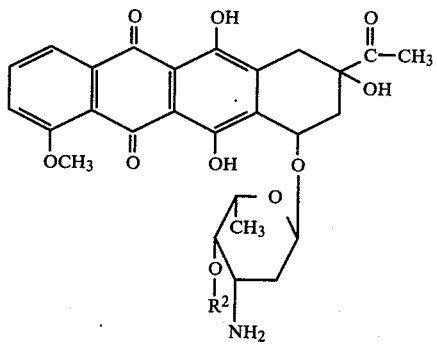

wherein R² is alkyloxyethyl in which the alkyl portion has from 1 to 8 carbon atoms inclusive, cyclohexyloxyethyl, tetrahydrofuranyl, 6-methoxytetrahydropyranyl, 6-carbomethoxytetrahydropyranyl or 6-acetoxymethyltetrahydropyranyl, or a nontoxic acid addition salt thereof.

* * * * *

UNITED STATES PATENT AND TRADEMARK OFFICE
CERTIFICATE OF CORRECTION

PATENT NO. : 4,303,785

DATED : December 1, 1981

INVENTOR(S) : Hamao Umezawa; Tomio Takeuchi; Hiroshi Naganawa; Kuniaki Tatsuta

It is certified that error appears in the above-identified patent and that said Letters Patent are hereby corrected as shown below:

In Claim 15, line 63, insert-- 6-carbomethoxytetrahydro-pyranyl-- after "6-methoxytetrahydropyranyl,".

Signed and Sealed this

Ninth Day of March 1982

[SEAL]

Attest:

Attesting Officer

GERALD J. MOSSINGHOFF

Commissioner of Patents and Trademarks